US010933429B2

United States Patent
Piyasena et al.

(10) Patent No.: US 10,933,429 B2
(45) Date of Patent: Mar. 2, 2021

(54) SEPARATION OF NANOPARTICLES VIA ACOUSTOFLUIDIC FLOW RELOCATION

(71) Applicant: NEW MEXICO TECH UNIVERSITY RESEARCH PARK CORPORATION, Socorro, NM (US)

(72) Inventors: Menake Piyasena, Albuquerque, NM (US); Gayatri P. Gautam, Socorro, NM (US)

(73) Assignee: NEW MEXICO TECH UNIVERSITY RESEARCH PARK CORPORATION, Socorro, NM (US)

( * ) Notice: Subject to any disclaimer, the term of this patent is extended or adjusted under 35 U.S.C. 154(b) by 0 days.

(21) Appl. No.: 15/919,886

(22) Filed: Mar. 13, 2018

(65) Prior Publication Data

US 2018/0264482 A1   Sep. 20, 2018

Related U.S. Application Data

(60) Provisional application No. 62/470,614, filed on Mar. 13, 2017.

(51) Int. Cl.
*B03B 5/02* (2006.01)
*B01L 3/00* (2006.01)
(Continued)

(52) U.S. Cl.
CPC .......... *B03B 5/02* (2013.01); *A61M 1/3678* (2014.02); *B01L 3/502753* (2013.01);
(Continued)

(58) Field of Classification Search
CPC ......... G01N 1/4094; G01N 2015/1081; G01N 2015/149; B01L 3/502753; B01L 3/502761; B01L 3/502769; B01L 3/502776; B01L 2200/0652; B01L 2300/0867; B01L 2400/0436; B01L 2400/0439; B03B 5/00; B03B 5/02; A61M 1/3678; B01D 21/283
See application file for complete search history.

(56) References Cited

U.S. PATENT DOCUMENTS 8,266,951 B2 *  9/2012  Kaduchak .......... G01N 15/1404
                                              73/61.75
8,387,803 B2 *  3/2013  Thorslund ......... B01L 3/502761
                                                209/552
(Continued)

OTHER PUBLICATIONS

Akbulut O et al., "Separation of nanoparticles in aqueous multiphase systems through centrifugation", Nano Lett. Aug 8, 2012;12(8):4060-4. doi: 10.1021/nl301452x. Epub Jul. 6, 2012.
(Continued)

*Primary Examiner* — Joseph C Rodriguez
(74) *Attorney, Agent, or Firm* — Wilson Sonsini Goodrich & Rosati

(57) ABSTRACT

The present disclosure describes a method of separating particles using a combination of acoustophoresis and acoustic fluid relocation. The disclosure also describes a microfluidic device that can be used to separate particles using a combination of acoustophoresis and acoustic fluid relocation. The disclosure describes methods of separating nanoparticles, microparticles, nanoparticles from microparticles, and micron-sized particles from sub-micron-sized particles.

19 Claims, 22 Drawing Sheets

(51) Int. Cl.
  G01N 33/49 (2006.01)
  A61M 1/36 (2006.01)
(52) U.S. Cl.
  CPC ... *G01N 33/491* (2013.01); *A61M 2205/0244* (2013.01); *B01L 2200/0647* (2013.01); *B01L 2400/0436* (2013.01)

(56) References Cited

U.S. PATENT DOCUMENTS

| | | | | |
|---|---|---|---|---|
| 9,513,205 | B2* | 12/2016 | Yu | B03C 1/288 |
| 9,656,263 | B2* | 5/2017 | Laurell | G01N 33/5005 |
| 9,670,477 | B2* | 6/2017 | Lipkens | C12M 47/04 |
| 9,827,511 | B2* | 11/2017 | Lipkens | B01D 21/283 |
| 9,835,540 | B2* | 12/2017 | Yu | B03C 1/288 |
| 2009/0042310 | A1* | 2/2009 | Ward | G01N 15/1404 436/154 |
| 2009/0277845 | A1* | 11/2009 | Sheen | B01L 3/502753 210/748.01 |
| 2010/0126922 | A1* | 5/2010 | Takahashi | B01D 21/283 210/201 |
| 2011/0154890 | A1* | 6/2011 | Holm | B01D 21/283 73/61.75 |
| 2014/0008307 | A1* | 1/2014 | Guldiken | B01L 3/502761 210/748.05 |
| 2015/0160116 | A1* | 6/2015 | Yu | B03C 1/288 435/173.9 |
| 2017/0232439 | A1* | 8/2017 | Suresh | G01N 15/1056 435/30 |

OTHER PUBLICATIONS

Antfolk M et al., "Continuous flow microfluidic separation and processing of rare cells and bioparticles found in blood—A review", Anal Chim Acta. May 1, 2017;965:9-35. doi: 10.1016/j.aca.2017.02.017. Epub Feb. 20, 2017.
Augustsson, Per et al. "Microfluidic, label-free enrichment of prostate cancer cells in blood based on acoustophoresis." Analytical chemistry vol. 84,18 (2012): 7954-62. doi:10.1021/ac301723s.
Austin Suthanthiraraj PP, Piyasena ME, Woods TA, et al. One-dimensional acoustic standing waves in rectangular channels for flow cytometry. Methods (San Diego, Calif.). Jul. 2012;57(3):259-271. DOI: 10.1016/j.ymeth.2012.02.013.
Chen, Chihchen et al. "Microfluidic isolation and transcriptome analysis of serum microvesicles." Lab on a chip vol. 10,4 (2010): 505-11. doi:10.1039/b916199f.
Deshmukh, Sameer et al., "Acoustic radiation forces at liquid interfaces impact the performance of acoustophoresis", The Royal Society of Chemistry, 2014, Lab Chip, pp. 1-7.
Di Carlo, Dino et al. "Continuous inertial focusing, ordering, and separation of particles in microchannels." Proceedings of the National Academy of Sciences of the United States of America vol. 104,48 (2007): 18892-7. doi:10.1073/pnas.0704958104.
Didar, Tohid Fatanat et al., "Separation of rare oligodendrocyte progenitor cells from brain using a high-throughput multilayer thermoplastic-based microfluidic device",Biomaterials, 2013, 34, 5588-5593.
Ferraz, Natalia et al., "Procoagulant Behavior and Platelet Microparticle Generation on Nanoporous Alumina", Biomater. Appl, 2010, 24, 675-692.
Gascoyne, Peter R C et al. "Isolation of rare cells from cell mixtures by dielectrophoresis." Electrophoresis vol. 30,8 (2009): 1388-98. doi:10.1002/elps.200800373.
Gor'kov, L.P., "On the Forces Acting on Small Particle in an Acoustical Field in an Ideal Fluid", Soviet Physics-Doklady, 1962, 6, 773-775.
Hammarstrom, B et al., "Seed particle-enabled acoustic trapping of bacteria and nanoparticles in continuous flow systems" , Lab Chip, 2012, 12, 4296-4304.
Johansson, L et al, "Effective mixing of laminar flows at a density interface by an integrated ultrasonic transducer", Lab Chip, 2009, 9, 297-304.
Lamparski HG et al., "Production and characterization of clinical grade exosomes derived from dendritic cells", Journal of Immunological Methods, vol. 270, Issue 2, Dec. 15, 2002, pp. 211-226.
Lenshof A et al., "Acoustofluidics 5: Building microfluidic acoustic resonators", Lab Chip. Feb. 21, 2012;12(4):684-95. doi: 10.1039/c1lc20996e. Epub Jan. 16, 2012.
Liu, Kelvin J. et al., "Decoding Circulating Nucleic Acids in Human Serum Using Microfluidic Single Molecule Spectroscopy" J. Am. Chem. Soc. 2010, 132, 16, 5793-5798.
Morgan, H et al. "Separation of submicron bioparticles by dielectrophoresis." Biophysical journal vol. 77,1 (1999): 516-25. doi:10.1016/S0006-3495(99)76908-0.
Ohlsson, Pelle et al., "Integrated Acoustic Separation, Enrichment, and Microchip Polymerase Chain Reaction Detection of Bacteria from Blood for Rapid Sepsis Diagnostics", Anal. Chem. 2016, 88, 19, 9403-9411.
Petersson F et al., "Free flow acoustophoresis: microfluidic-based mode of particle and cell separation", Anal Chem. Jul. 15, 2007;79(14):5117-23. Epub Jun. 15, 2007.
Petersson, F et al,, "Separation of lipids from blood utilizing ultrasonic standing waves in microfluidic channels", Analyst. Oct. 2004;129(10):938-43. Epub Aug. 18, 2004.
Petersson, Filip et al., "Carrier Medium Exchange through Ultrasonic Particle Switching in Microfluidic Channels", Anal. Chem, 2005, 77, 1216-1221.
Piyasena, Menake E, and Steven W Graves. "The intersection of flow cytometry with microfluidics and microfabrication." Lab on a chip vol. 14,6 (2014): 1044-59. doi:10.1039/c3lc51152a.
Piyasena, Menake E. et al., "Multinode Acoustic Focusing for Parallel Flow Cytometry", Anal. Chem. 2012, 84, 4, 1831-1839.
Raddatz MS et al., "Enrichment of cell-targeting and population-specific aptamers by fluorescence-activated cell sorting", Angew Chem Int Ed Engl. 2008;47(28):5190-3. doi: 10.1002/anie.200800216.
Shields, C Wyatt 4th et al. "Microfluidic cell sorting: a review of the advances in the separation of cells from debulking to rare cell isolation." Lab on a chip vol. 15,5 (2015): 1230-49. doi:10.1039/c4lc01246a.
Tauro BJ et al., "Comparison of ultracentrifugation, density gradient separation, and immunoaffinity capture methods for isolating human colon cancer cell line LIM1863-derived exosomes", Methods. Feb. 2012;56(2):293-304. doi: 10.1016/j.ymeth.2012.01.002. Epub Jan. 21, 2012.
Van der Pol, E et al., "Classification, functions, and clinical relevance of extracellular vesicles",Pharmacol Rev. Jul. 2012;64(3):676-705. doi: 10.1124/pr.112.005983. Epub Jun. 21, 2012.
Weigl, B.H et al., "Diffusion-Based Optical Chemical Detection in Silicon Flow Structures", Proc uTas, 1996, 174-184.
Weigl, B.H. et al.,"Microfluidic Diffusion-Based Separation and Detection", Science 1999, 283, 346-347.

* cited by examiner

SEPARATION OF NANOPARTICLES VIA ACOUSTOFLUIDIC FLOW RELOCATION

CROSS REFERENCE

This Application claims the benefit of U.S. Provisional Application No. 62/470,614, filed Mar. 13, 2017, which is incorporated herein by reference in its entirety.

GOVERNMENT RIGHTS

The invention was made with government support under Grant Number P20GM103451 by the National Institutes of Health; Contract Number DE-AC52-06NA25396 (Los Alamos National Laboratory) and Contract Number DE-AC04-94AL85000 (Sandia National Laboratories) by the Department of Energy. The government has certain rights in the invention.

BACKGROUND

Acoustophoresis is a method for suspending matter in a medium using acoustic radiation pressure from intense sound waves in the medium. Acoustophoresis can be used to isolate and enrich particles that are greater than 1 μm in size. Methods of isolating and enriching particles that are less than 1 μm in size (e.g., viruses, bacteria, exosomes, DNA, and blood cells) can be useful in clinical applications.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a method of separating a mixture of particles, the method comprising:
1) suspending the mixture of particles in a flow stream;
2) flowing the flow stream through a channel; and
3) subjecting the flow stream in the channel to a standing acoustic wave field, wherein the standing acoustic wave field subjects the flow stream to acoustophoresis and acoustic fluid relocation.

In some embodiments, the invention provides a device comprising:
1) a base slide, wherein the base slide comprises a top surface;
2) a connector, wherein the connector is attached to the top surface of the base slide;
3) an electrical component that produces an acoustic standing wave field, wherein the electrical component is attached to the top surface of the base slide;
4) a plate, wherein the plate comprises a top surface and a bottom surface, wherein the bottom surface of the plate is connected to the connector and the electrical component so that the plate is layered above the top surface of the base slide, wherein the top surface of the plate comprises a channel with an inlet end and an outlet end, wherein the inlet end comprises three inlet ports and the outlet end comprises three outlet ports, wherein the electrical component is positioned to transmit the acoustic standing wave field to the channel; and
5) a coverslide, wherein the coverslide is layered on the top surface of the plate, wherein the coverslide comprises six holes, wherein three holes are aligned with the three inlet ports and three holes are aligned with the three outlet ports.

In some embodiments, the method provides a method of separating a mixture of particles, the method comprising:
1) suspending the mixture of particles in a flow stream;
2) flowing the flow stream through a channel of a device, the device comprising:
    a) a base slide, wherein the base slide comprises a top surface;
    b) a connector, wherein the connector is attached to the top surface of the base slide;
    c) an electrical component that produces an acoustic standing wave field, wherein the electrical component is attached to the top surface of the base slide;
    d) a plate, wherein the plate comprises a top surface and a bottom surface, wherein the bottom surface of the plate is connected to the connector and the electrical component so that the plate is layered above the top surface of the base slide, wherein the top surface of the plate comprises a channel with an inlet end and an outlet end, wherein the inlet end comprises three inlet ports and the outlet end comprises three outlet ports, wherein the electrical component is positioned to transmit the acoustic standing wave field to the channel; and
    e) a coverslide, wherein the coverslide is layered on the top surface of the plate, wherein the coverslide comprises six holes, wherein three holes are aligned with the three inlet ports and three holes are aligned with the three outlet ports;
3) subjecting the flow stream in the channel to the standing acoustic wave field, wherein the standing acoustic wave field subjects the flow stream to acoustophoresis and acoustic fluid relocation.

BRIEF DESCRIPTION OF THE FIGURES

FIG. 4 PANEL B shows the bottom view of the microfluidic device with the attached transducer and the PDMS supports.

FIG. 10 PANEL B shows the flow profiles of the 1×PBS solution and the 2.5 μM fluorescein solution. FIG. 10 PANEL C shows the relocation of the 1×PBS and 2.5 μM fluorescein solution in the presence of an acoustic wave field. FIG. 10 PANEL D shows the flow profiles of the relocated streams.

FIG. 11 PANEL B shows the switching of streams upon application of an acoustic field.

FIG. 12 PANEL B shows an epi-fluorescence micrograph showing the relocation of lateral 0.1×PBS streams and a 2.5 µM fluorescein stream upon application of an acoustic force. FIG. 12 PANEL C shows an epi-fluorescence micrograph of the laminar flow of three streams of 2.5 µM fluorescein in de-ionized water as the central stream, and de-ionized water as the lateral streams in the absence of an acoustic force. FIG. 12 PANEL D shows an epi-fluorescence micrograph showing that there was no relocation of the 2.5 µM fluorescein solution and de-ionized water streams upon applying an acoustic force.

FIG. 14 PANEL B shows the relocation of the sub-micron particles to the lateral stream. FIG. 14 PANEL C shows the concentration of sub-micron particles in the lateral and central streams before and after fluid relocation.

FIG. 15 PANEL B shows a line scan analysis of the fluorescent flow stream profile. FIG. 15 PANEL C shows that, in the presence of an acoustic field, the 100 nm nanoparticles were moved to the lateral stream while the 2 µm microparticles remained in the central stream. FIG. 15 PANEL D shows the background-corrected line scan profile of the fluorescence image, which shows the appearance of two fluorescence streaks from the flow of nanoparticles.

FIG. 16 PANEL B shows the line scan image demonstrating the width of the central stream. FIG. 16 PANEL C shows lipid vesicles with an average diameter of 200 nm split into two lateral streams via acoustic fluid relocation. FIG. 16 PANEL D shows the line scan image of the two lateral streams after acoustic fluid relocation.

FIG. 17 PANEL B shows an epi-fluorescence micrograph, where the 0.25 µm particles are dragged to the lateral stream along with the fluid, and the 2.07 µm particles are focused to the central stream in the presence of an acoustic wave field. FIG. 17 PANEL C shows the flow cytometry scatter dot plot for the central stream with acoustics turned off. FIG. 17 PANEL D shows the flow cytometry scatter dot plot for the central stream with acoustics turned on. FIG. 17 PANEL E shows the flow cytometry scatter dot plot for the lateral stream with acoustics turned on.

FIG. 18 PANEL B shows the separation of 2.07 µm and 0.84 µm particles. FIG. 18 PANEL C shows the separation of 4.24 µm and 0.84 µm particles. FIG. 18 PANEL D shows the separation of 11.0 µm and 0.84 µm particles. The two gated regions indicate the percentages of particles.

FIG. 19 PANEL B shows a flow cytometry scatter plot of the central stream in the presence of acoustics for the mixture containing 5.1 µm and 11.0 µm particles. FIG. 19 PANEL C shows a flow cytometry scatter plot of the lateral stream in the presence of acoustics for the mixture containing 5.1 µm and 11.0 µm particles. FIG. 19 PANEL D shows a flow cytometry scatter plot of the central stream of a second run in the absence of acoustics. FIG. 19 PANEL E shows a flow cytometry scatter plot of the central stream of a second run in the presence of acoustics. FIG. 19 PANEL F shows a flow cytometry scatter plot of the lateral stream of a second run in the presence of acoustics.

FIG. 20 PANEL B shows that the central stream had 25.20% of 2.07 µm particles and 73.87% of 11.0 µm in the presence of acoustics. FIG. 20 PANEL C shows that the lateral stream had 99.57% of 2.07 µm particles and 0.00% of 11.0 µm in the presence of acoustics.

FIG. 21 PANEL B shows a flow cytometry scatter plot of the lateral stream in the presence of acoustics. FIG. 21 PANEL C shows a flow cytometry scatter plot of the central stream in the absence of acoustics. FIG. 21 PANEL D shows a flow cytometry scatter plot of the central stream in the presence of acoustics.

FIG. 22 PANEL B shows that the lateral stream had 82.53% of 5.1 µm particles and 12.00% of 11.0 µm particles in the presence of acoustics. FIG. 22 PANEL C shows that the central stream had 96.86% of 5.1 µm particles and 0.01% of 11.0 µm particles in the absence of acoustics. FIG. 22 PANEL D shows that the central stream had 46.36% of 5.1 µm particles and 52.73% of 11.0 µm particles in the absence of acoustics.

DETAILED DESCRIPTION

Acoustophoresis, or acoustic levitation, is a method for suspending matter in a medium using acoustic radiation pressure from intense sound waves in the medium. Acoustophoresis is a gentle, label-free, non-contact, and high throughput cell and particle separation technique. Acoustophoresis can be used to isolate and enrich particles that are greater than 1 µm in size.

Particles in a suspension exposed to an acoustic standing wave field are affected by a radiation force. In the presence of an acoustic standing wave field, particles suspended in a microfluidic flow experience a primary axial acoustic force, and cells and particles can be manipulated continuously using the acoustic force. The magnitude of the primary axial force is proportional to a particle's volume; larger particles experience greater acoustic forces than smaller particles experience. The radiation force causes the particles to move in the sound field if the acoustic properties of the particles differ from the acoustic properties of the surrounding medium.

In the presence of resonance acoustic standing waves, particles in a resonant chamber (e.g., a microfluidic channel) can experience primary acoustic forces. The acoustic force experienced by a particle depends on the size of the particle, acoustic wavelength, radiation pressure, and acoustic contrast factor, as given by equation (1):

$$F = -\left(\frac{\pi p_0^2 V_p \beta_m}{2\lambda}\right)\phi(\beta, \rho)\sin 2kx, \quad (1)$$

wherein: $\rho_o$ represents the amplitude of the radiation pressure, $V_p$ represents the volume of the particle, $\beta$ represents compressibility, $\phi$ represents the acoustic contrast factor, k represents the wave number, x represents the distance to the particle from the pressure node, $\lambda$ represents the wavelength of acoustic radiation, and m represents the medium. As the equation suggests, larger particles experience stronger acoustic force.

The acoustic contrast factor determines the position of particle focusing, as shown by equation (2):

$$\phi(\beta, \rho) = \frac{5\rho_p - 2\rho_m}{2\rho_p + \rho_m} - \frac{\beta_p}{\beta_m}. \quad (2)$$

The acoustic contrast factor depends on the compressibility and density of a particle and the medium. A particle with a positive contrast factor is focused on the pressure nodal plane of a resonant chamber. A particle with a negative contrast factor is focused on the pressure anti-node. When the size of a particle becomes smaller, about 1 μm or less, the primary acoustic force on a particle is weak, and acoustic manipulation of the particle becomes challenging. The magnitude of particle movement can also depend on factors such as the acoustic pressure amplitude and frequency of the sound wave. The direction the particles are moved in depends on the density and compressibility of the particles and the liquid medium.

Figure 1:
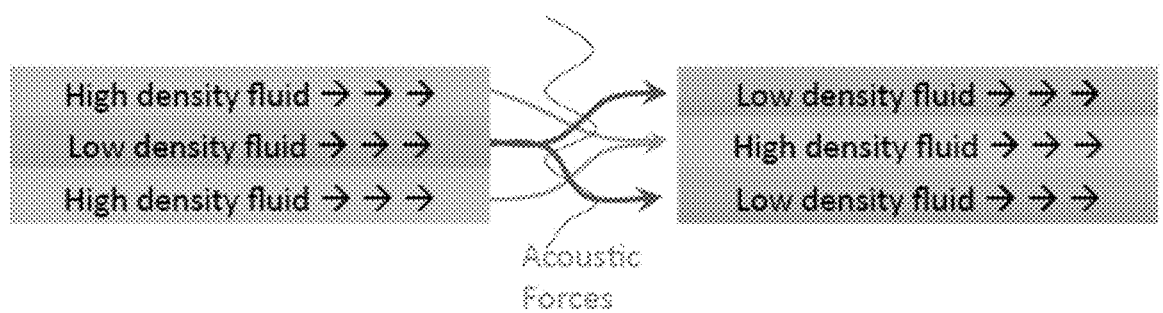
FIG. 1 illustrates the use of acoustic forces on fluid interfaces to move a higher density fluid to the center of a fluid stream.

FIG. 1 illustrates the use of acoustic forces on fluid interfaces to move a higher density fluid to the center of a fluid stream.

Acoustophoresis Combined with Acoustic Fluid Relocation to Separate Particles

The disclosure describes methods of manipulating and separating particles smaller than 1 μm by combining acoustophoresis and acoustic fluid relocation. The disclosure describes the use of acoustic forces to relocate parallel laminar flow streams of two impedance mismatched fluids. When a mixture of sub-micrometer sized (diameter or mean diameter<1 μm) particles and micrometer sized (diameter or mean diameter>1 μm) particles suspended in a low impedance fluid is used as the central stream, the micrometer sized particles experience strong acoustic forces and remain in the center stream. The sub-micrometer sized particles are dragged to the two sides along with the low impedance fluid. Combining these two processes allows for the separation of sub-micron-sized particles from micron-sized particles.

In some embodiments, the invention separates particles in a continuous flow. In some embodiments, the invention directs the separated stream of particles into a flow-through analytical system. In some embodiments, continuous flow separation of particles can be conducted using electrophoresis, dielectrophoresis, or magnetic separation.

The disclosed invention can separate and enrich nanometer-sized particles (i.e., nanoparticles), micrometer-sized particles (i.e., microparticles), or cells in a binary mixture consisting of nanoparticles and larger particles. In some embodiments, the combination of implementing acoustic forces on microparticles and fluid relocation forces (i.e., drag forces) on nanoparticles can isolate nanoparticles faster than is possible by other methods.

Fluid relocation is dependent on the impedance of liquids. In some embodiments, the invention can reposition two liquids with different acoustic impedances that are flowing adjacent to each other in a microfluidic device in the presence of a resonance acoustic standing wave field. In some embodiments, the invention can use acoustic forces on fluid interfaces to move a fluid with higher impedance to the center of the fluid stream. In some embodiments, the invention can exchange the positions of two parallel fluid streams by applying a proper acoustic switching frequency. In some embodiments, the invention can exchange the positions of two parallel fluid streams by applying a proper acoustic switching frequency even if the impedance difference of the two fluids is very small. In some embodiments, the invention can use acoustic flow switching to mix fluids in a microfluidic device.

A fluid stream can have an acoustic impedance of at least about $1.4 \times 10^6$ Pa s/m. In some embodiments, two parallel fluid streams can have different acoustic impedances. In some embodiments, one fluid stream can have an acoustic impedance of about $1.4 \times 10^6$ Pa s/m and a second fluid stream can have an acoustic impedance that is greater than about $1.4 \times 10^6$ Pa s/m.

In some embodiments, the invention can use acoustic flow switching to sort labelled particles. In some embodiments, the invention can use a combination of acoustic flow switching and acoustic focusing to separate particles. In some embodiments, in the invention can use a combination of acoustic flow switching and acoustic focusing to separate nanoparticles from microparticles. In some embodiments, the disclosed invention can manipulate the position of moving nanometer-sized lipid vesicles.

In some embodiments, the invention utilizes fluid drag created by acoustic forces to manipulate nanoparticles. In some embodiments, three laminar flow streams flowing parallel to one another can be used to create a nanoparticle separation system. In some embodiments, the disclosed invention can be used to purify microparticles from any debris that is smaller than the particles of interest.

In some embodiments, the microparticles are positioned near the pressure node, and require less force to overcome fluid drag forces. In some embodiments, the invention can use less power than purifying microparticles in sheath fluid using acoustic focusing. In some embodiments, the invention works at a higher flow rate than conventional methods of separating nanoparticles from microparticles.

The fluid drag forces of the invention are higher than the primary acoustic forces acting on the nanoparticles. In some embodiments, the invention can be used to relocate nanoparticles into a lateral flow, while larger particles are focused at the center of the flow stream. In some embodiments, the invention uses an acoustic frequency near that of resonance standing waves. In some embodiments, the invention can be used to isolate virus-type particles from a cell sample. In some embodiments, the invention can be used to isolate red blood cells, white blood cells, bacteria, viruses, exosomes, lipid particles, and cell debris.

In some embodiments, a microfluidic channel is equipped with branched inlets and outlets, which are utilized to transfer particles from the sample fluid stream to a carrier stream. In some embodiments, the sample fluid is infused via the lateral inlets, and the carrier (e.g., biological buffer, de-ionized water, etc) is introduced via a central inlet. In some embodiments, the carrier is a salt solution. In some embodiments, the carrier is a salt solution made by mixing at least one inorganic salt in de-ionized water. In some embodiments, applying an acoustic standing wave field moves the larger particles of the mixture to the central fluid stream, and retains the smaller particles in the lateral fluid stream.

In some embodiments, the acoustic impedance of the central fluid is greater than the acoustic impedance of the lateral fluid. In some embodiments, the acoustic impedance of the central fluid is the same as the acoustic impedance of the lateral fluid. In some embodiments, the acoustic impedance of the lateral fluid is higher than the acoustic impedance of the central fluid. In some embodiments, the acoustic impedance of the lateral fluid is higher than the acoustic impedance of the central fluid, and the presence of an acoustic standing wave field switches the positions of the lateral fluid and the central fluid (i.e., acoustic fluid relocation).

In some embodiments, the lateral fluid and central fluid can have different impedances. In some embodiments, the lateral fluid and central fluid can have a difference in impedance of about $0.01 \times 10^6$ Pa s/m, about $0.05 \times 10^6$ Pa s/m, about $0.1 \times 10^6$ Pa s/m, about $0.15 \times 1.0^4$ Pa s/m, about $0.2 \times 10^6$ Pa s/m, about $0.25 \times 10^6$ Pa s/m, about $0.3 \times 10^6$ Pa s/m, about $0.35 \times 10^6$ Pa s/m, about $0.4 \times 10^6$ Pa s/m, about $0.45 \times 10^6$ Pa s/m, or about $0.5 \times 10^6$ Pa s/m.

In some embodiments, the disclosed invention is used to separate a mixture of sub-micrometer sized particles and micrometer sized particles suspended in a fluid. In some embodiments, the sub-micrometer sized particles to be separated are less than 1 μm in diameter or mean diameter. In some embodiments, the sub-micrometer sized particles to be separated are about 0.1 μm, about 0.15 μm, about 0.2 μm, about 0.25 μm, about 0.3 μm, about 0.35 μm, about 0.4 μm, about 0.45 μm, about 0.5 μm, about 0.55 μm, about 0.6 μm, about 0.65 μm, about 0.7 μm, about 0.75 μm, about 0.8 μm, about 0.85 μm, about 0.9 μm, or about 0.95 μm in diameter or mean diameter. In some embodiments, the sub-micrometer sized particles to be separated are about 0.25 μm, about 0.55 μm, about 0.85 μm in diameter or mean diameter.

In some embodiments, the nanoparticles are about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 nm in diameter or mean diameter.

In some embodiments, the nanoparticles are synthetic nanoparticles. In some embodiments, nanoparticles are lipid vesicles. In some embodiments, the nanoparticles are silicate, zinc oxide, silicon dioxide, silver, gold, or iron nanoparticles. In some embodiments, the nanoparticles are bacteria, such as gram-negative bacteria (e.g., *E. coli*). In some embodiments, the nanoparticles are exosomes, virus particles, or lipid particles.

In some embodiments, the microparticles are more than 1 μm in diameter or mean diameter. In some embodiments, the microparticles are about 1 μm, about 1.5 μm, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 9.5 μm, or about 10 μm in diameter or mean diameter. In some embodiments, the microparticles are 2 μm in diameter or mean diameter. In some embodiments, the microparticles are about 3 μm in diameter or mean diameter.

In some embodiments, the microparticles are red blood cells. In some embodiments, the microparticles are bacteria, large exosomes, white blood cells, or mammalian cells.

In some embodiments, the binary mixture is prepared using de-ionized water. In some embodiments, the binary mixture is prepared using a buffer solution. In some embodiments, the binary mixture can be prepared using an acidic buffer solution or a basic buffer solution. In some embodiments, the binary mixture can be prepared using a buffer, such as glycine-HCl, sodium acetate, buffered saline (e.g., phosphate-buffered saline (PBS), Tris-buffered saline (TBS), Tris-NaCl-polysorbate 20 (TNT), or PBS and polysorbate 20 (PBT)). In some embodiments, the binary mixture can be prepared using de-ionized water. In some embodiments, the binary mixture can be prepared using non-buffered salt solutions with different salt concentrations, for example, about 0.05 mM NaCl, about 0.1 mM NaCl, or about 0.15 mM NaCl.

The binary mixture to be separated can comprise a concentration of particles of about 10,000 particles/mL to about 500,000 particles/mL. In some embodiments, the binary mixture to be separated can comprise a concentration of particles of about 10,000 particles/mL, about 15,000 particles/mL, about 20,000 particles/mL, about 25,000 particles/mL, about 30,000 particles/mL, about 35,000 particles/mL, about 40,000 particles/mL, about 45,000 particles/mL, about 50,000 particles/mL, about 55,000 particles/mL, about 60,000 particles/mL, about 65,000 particles/mL, about 70,000 particles/mL, about 75,000 particles/mL, about 80,000 particles/mL, about 85,000 particles/mL, about 90,000 particles/mL, about 95,000 particles/mL, about 100,000 particles/mL, about 110,000 particles/mL, about 120,000 particles/mL, about 130,000 particles/mL, about 140,000 particles/mL, about 150,000 particles/mL, about 160,000 particles/mL, about 170,000 particles/mL, about 180,000 particles/mL, about 190,000 particles/mL, about 200,000 particles/mL, about 225,000 particles/mL, about 250,000 particles/mL, about 275,000 particles/mL, about 300,000 particles/mL, about 325,000 particles/mL, about 350,000 particles/mL, about 375,000 particles/mL, about 400,000 particles/mL, about 425,000 particles/mL, about 450,000 particles/mL, about 475,000 particles/mL, or about 50,000 particles/mL. In some embodiments, the binary mixture to be separated comprises about 50,000 particles/mL to about 100,000 particles/mL.

Binary mixtures can be separated such that each component separated from the mixture is at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Microfluidic Device

The disclosure also describes a microfluidic device that is used to purify and enrich a binary mixture of nanoparticles of microparticles. In some embodiments, a microfluidic device can be made of silicon glass. In some embodiments, a microfluidic device can be made of silicon and glass. In some embodiments, a microfluidic device can be made of metals, for example, aluminum or aluminum allows. In some embodiments, a microfluidic device can be made of hard polymers, for example, poly methyl methacrylate (PMMA) or polystyrene (PS). In some embodiments, a silicon wafer can be photo-patterned and etched, and a borosilicate glass slide can be bonded to the top surface of the etched wafer. In some embodiments, a silicon wafer can be photo-patterned with positive photoresist and etched using deep reactive ion etching. In some embodiments, the silicon wafer can be etched using chemical etching. In some embodiments, a borosilicate glass slide can be anodically bonded to the top surface of the etched wafer.

A microfluidic device can be prepared using a silicon wafer about 50 mm, about 60 mm, about 70 mm, about 80 mm, about 90 mm, about 100 mm, about 110 mm, about 120 mm, about 130 mm, about 140 mm, about 150 mm, about 160 mm, about 170 mm, about 180 mm, about 190 mm, or about 200 mm in diameter. A microfluidic device can be prepared using a silicon wafer about 200 mm, about 225 mm, about 250 mm, about 275 mm, about 300 mm, about 325 mm, about 350 mm, about 375 mm, about 400 mm, about 425 mm, or about 450 mm in diameter. In some embodiments, a microfluidic device can be prepared using a silicon wafer about 100 mm in diameter.

A microfluidic device can be prepared using a silicon wafer about 200 µm, about 225 µm, about 250 µm, about 275 µm, about 300 µm, about 325 µm, about 350 µm, about 375 µm, about 400 µm, about 425 µm, about 450 µm, about 475 µm, about 500 µm, about 525 µm, about 550 µm, about 575 µm, about 600 µm, about 625 µm, about 650 µm, about 675 µm, about 700 µm, about 725 µm, about 750 µm, about 775 µm, about 800 µm, about 825 µm, about 850 µm, about 875 µm, about 900 µm, about 925 µm, about 950 µm, about 975 µm, or about 1000 µm thick.

In some embodiments, the microfluidic device comprises one main channel with inlets and outlets. In some embodiments, the microfluidic device comprises more than one main channel with inlets and outlets. In some embodiments, the microfluidic device comprises trifurcated inlets and outlets. In some embodiments, the microfluidic device can use silicone tubing to allow flow of a solution into the inlet and out of the outlet.

The microfluidic device can have channels that are about 50 µm to about 300 µm wide. In some embodiments, the microfluidic device can have channels that are about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, or about 300 µm wide. In some embodiments, the microfluidic device can have channels that are about 150 µm wide. In some embodiments, the microfluidic device can have channels that are about 200 µm wide. In some embodiments, the microfluidic device can have channels that are about 250 µm wide.

The microfluidic device can have channels that are about 20 µm to about 200 µm deep. In some embodiments, the microfluidic device can have channels that are about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm deep. In some embodiments, the microfluidic device can have channels that are about 80 µm deep. In some embodiments, the microfluidic device can have channels that are about 100 µm deep. In some embodiments, the microfluidic device can have channels that are about 120 µm deep.

The microfluidic device can have two lateral inlets that can maintain a stream of about 10 µm to about 100 µm in width. In some embodiments, the microfluidic device can have two lateral inlets that can maintain a stream of about 10 µm, about 20 µm, about 30 µm, about 40 µm, about 50 µm, about 60 µm, about 70 µm, about 80 µm, about 90 µm, or about 100 µm. In some embodiments, the microfluidic device can have two lateral inlets that can maintain a stream of about 30 µm. In some embodiments, the microfluidic device can have two lateral inlets that maintain a stream of about 40 µm. In some embodiments, the microfluidic device can have two lateral inlets that can maintain a stream of about 50 µm. In some embodiments, the microfluidic device can have lateral inlets that can maintain a stream width of about 100 µm, about 150 µm, about 200 µm, about 250 urn, about 300 µm, about 350 µm, about 400 µm, about 450 µm, or about 500 µm.

The microfluidic device can have a central inlet that can maintain a stream of about 10 µm to about 100 µm in width. In some embodiments, the microfluidic device can have a central inlet that can maintain a stream of about 10 µm, about 20 µm, about 30 µm, about 40 µm, about 50 µm, about 60 µm, about 70 µm, about 80 µm, about 90 µm, or about 100 µm. In some embodiments, the microfluidic device can have a central inlet that can maintain a stream of about 30 µm. In some embodiments, the microfluidic device can have a central inlet that can maintain a stream of about 40 µm. In some embodiments, the microfluidic device can have a central inlet that can maintain a stream of about 50 µm. In some embodiments, the microfluidic device can have a central stream that can maintain a stream width of about 100 µm, about 150 µm, about 200 µm, about 250 µm, about 300 about 350 µm, about 400 µm, about 450 µm, or about 500 µm.

Standing acoustic waves can be generated using a piezoelectric transducer. In some embodiments, standing acoustic waves can be generated using a piezoelectric transducer that is about 3 cm long and about 0.5 cm wide. In some embodiments, the transducer is at least 5 mm×5 mm. The piezoelectric transducer can be glued underneath the channel of the microfluidic device.

The piezoelectric transducer can generate a resonance frequency, or a mean resonance frequency, of about 2 MHz to about 3.5 MHz. In some embodiments, the piezoelectric transducer can generate a resonance frequency, or a mean resonance frequency, of about 500 kHz to 10 MHz. In some embodiments, the piezoelectric transducer can generate a resonance frequency, or a mean resonance frequency, of about 2 MHz, about 2.1 MHz, about 2.2 MHz, about 2.3 MHz, about 2.4 MHz, about 2.5 MHz, about 2.6 MHz, about 2.7 MHz, about 2.8 MHz, about 2.9 MHz, about 3 MHz, about 3.1 MHz, about 3.2 MHz, about 3.3 MHz, about 3.4 MHz, about 3.4 MHz, about 3.5 MHz, about 3.6 MHz, about 3.7 MHz, about 3.8 MHz, about 3.9 MHz, or about 4 MHz. In some embodiments, the piezoelectric transducer can generate a resonance frequency of about 2.91 MHz. In some embodiments, the piezoelectric transducer can generate a resonance frequency, or a mean resonance frequency, of about 4 MHz, about 4.5 MHz, about 5 MHz, about 5.5 MHz, about 6 MHz, about 6.5 MHz, about 7 MHz, about 7.5 MHz, about 8 MHz, about 8.5 MHz, about 9 MHz, about 9.5 MHz, or about 10 MHz. In some embodiments, the resonance frequency, or a mean resonance frequency, of a piezoelectric transducer can be amplified using a radiofrequency (RF) amplifier.

The applied peak-to-peak voltage ($V_{pp}$) of the microfluidic device can be about 1 $V_{pp}$, about 2 $V_{pp}$, about 3 $V_{pp}$, about 4 $V_{pp}$, about 5 $V_{pp}$, about 6 $V_{pp}$, about 7 $V_{pp}$, about 8 $V_{pp}$, about 9 $V_{pp}$, about 10 $V_{pp}$, about 11 $V_{pp}$, about 12 $V_{pp}$, about 13 $V_{pp}$, about 14 $V_{pp}$, about 15 $V_{pp}$, about 16 $V_{pp}$, about 17 $V_{pp}$, about 18 $V_{pp}$, about 19 $V_{pp}$, about 20 $V_{pp}$, about 21 $V_{pp}$, about 22 $V_{pp}$, about 23 $V_{pp}$, about 24 $V_{pp}$, about 25 $V_{pp}$, about 26 $V_{pp}$, about 27 $V_{pp}$, about 28 $V_{pp}$, about 29 $V_{pp}$, or about 30 $V_{pp}$. In some embodiments, the $V_{pp}$ of the microfluidic device can be about 10 $V_{pp}$. In some embodiments, the $V_{pp}$ of the microfluidic device can be about 15 $V_{pp}$. In some embodiments, the $V_{pp}$ of the microfluidic device can be about 20 $V_{pp}$.

The microfluidic device of the disclosure can use a pump to control the flow rate of the lateral and central inlets. In some embodiments, the microfluidic device uses a syringe pump to control the flow rate of the lateral and central inlets. In some embodiments, the microfluidic device uses a peristaltic pump to control the flow rate of the lateral and central inlets.

The flow rate of the lateral and central inlets can be about 5 about 10 µL/min, about 15 µL/min, about 20 µL/min, about 25 µL/min, about 30 µL/min, about 35 µL/min, about 40 µL/min, about 45 about 50 µL/min, about 55 µL/min, about 60 µL/min, about 65 µL/min, about 70 µL/min, about 75 µL/min, about 80 µL/min, about 85 µL/min, about 90 µL/min, about 95 µL/min, or about 100 µL/min. In some embodiments, the flow rate of the lateral inlet is about 25 µL/min. In some embodiments, the flow rate of the central inlet is about 75 µL/min. In some embodiments, the flow rate of the later inlet is about 25 µL/min, and the flow rate of the central inlet is about 75 µL/min. In some embodiments, the flow rate of the lateral inlet is about 75 µL/min. In some embodiments, the flow rate of the central inlet is about 50 µL/min. In some embodiments, the flow rate of the lateral inlet is about 75 µL/min, and the flow rate of the central inlet is about 50 µL/min.

The particle streams collected from the lateral and central outlets can be analyzed to determine the composition of the particle streams and extent of particle separation. In some embodiments, flow cytometry measurements can be used to analyze the particle composition of the outlet streams. In some embodiments, flow cytometry measurements can be used to generate scatter dot plots to determine the particle composition of the outlet streams. In some embodiments, an epi-fluorescence microscope can be used to analyze the particle composition of the outlet streams. In some embodiments, an epi-fluorescence microscope equipped with a scientific complementary metal oxide-semiconductor (sC-MOS) camera can be used to analyze the particle composition of the outlet streams.

The microfluidic device of the disclosure can comprise a power source. In some embodiments, the microfluidic device comprises a direct current (DC) power source. In some embodiments, the microfluidic device comprises an alternating current (AC) power source. In some embodiments, the microfluidic device is connected to a battery.

Applications

Acoustic focusing of cells and particles is a technique that can be used in cytometric applications. Acoustic focusing can be implemented in microfluidic devices for purifying and enriching samples prior to analysis of the samples for various applications. In some embodiments, a purified or enriched sample can be integrated into a conventional flow cytometer for further analysis.

The acoustic manipulation of nanoparticles described herein can be used in clinical applications. In some embodiments, the invention can be used to separate and/or enrich viruses, bacteria, exosomes, DNA, and other nano-meter sized and sub-micrometer sized components from micrometer-sized components in biological fluids. In some embodiments, the sample that is separated and enriched has been centrifuged prior to being treated with methods of the disclosure. In some embodiments, the sample that is separated and enriched has not been centrifuged prior to being treated with methods of the disclosure. In some embodiments, the invention can be used to isolate clinically important nanometer-scale viruses, bacteria, and cellular components, such as exosomes or lipid particles from blood and other biological samples.

In some embodiments, the invention can be used to separate two different sizes of cells. In some embodiments, the invention can be used to separate two different sized cancer cells. In some embodiments, the invention can be used to separate cancer cells from healthy cells. In some embodiments, the invention can be used to separate MCF-7 cells from healthy cells. In some embodiments, the invention can be used to separate disease-infected cells from healthy cells. In some embodiments, the invention can be used to separate malaria-infected red blood cells from healthy red blood cells.

EXAMPLES

Example 1: Materials Used to Manufacture Microfluidic Devices

Silicon or glass wafers (100 mm diameter), an AZ® 9260 photoresist or any positive-type photoresist and developer, hexa-methyldisilazane (HMDS), SCHOTT Borofloat®-33 glass slides (75 mm×50 mm×1 mm), poly(dimethylsiloxane) (PDMS), silicone tubing (0.64 mm ID), and lead zirconate titanate (PZT) ceramic transducers were used. Acetone, phosphate-buffered saline (PBS) buffer tablets, NaCl, fluorescein sodium salt, group B red blood cells (B-RBCs), *E. coli*, and CountBright™ absolute counting beads were used.

Example 2: Fabrication of a Microfluidic Device

A study was performed with a silicon microfluidic device that was microfabricated with deep reactive ion etching. A 4 cm long, 200 µm wide, and 100 µm deep channel with a trifurcated inlet and outlet was used. An anodically-bonded borosilicate glass slide was used as the lid to enclose the microchannel. Silicone tubing was attached to pre-drilled holes on the lid, and was connected to syringe pumps. A piezoelectric transducer was glued to the bottom of the channel using epoxy glue. The assembled device was then mounted on a glass slide using PDMS slabs and double-sided tape.

Figure 2:
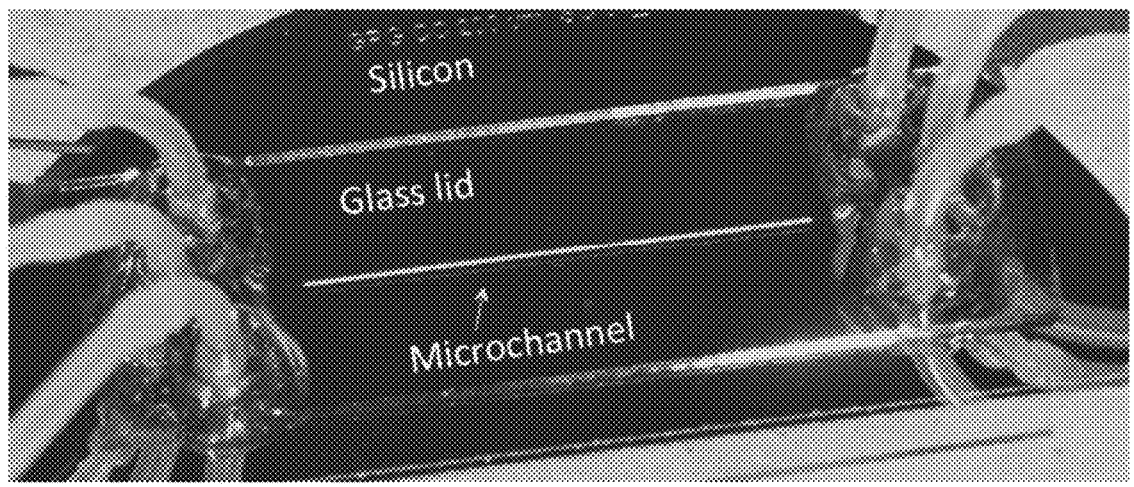
FIG. 2 shows the etched silicon channel enclosed with a glass lid.
Figure 3:
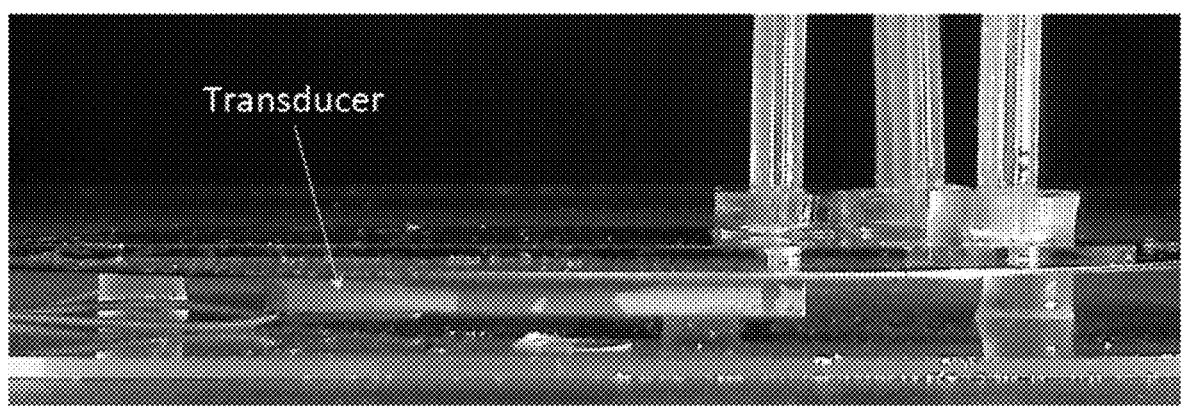
FIG. 3 shows the acoustic transducer glued to the back of the device using epoxy glue.

FIG. 2 shows the etched silicon channel enclosed with a glass lid. The silicone tubing served as a fluidic connector. FIG. 3 shows the acoustic transducer glued to the back of the device using epoxy glue.

Example 3: Fabrication of a Microfluidic Device

Figure 4:
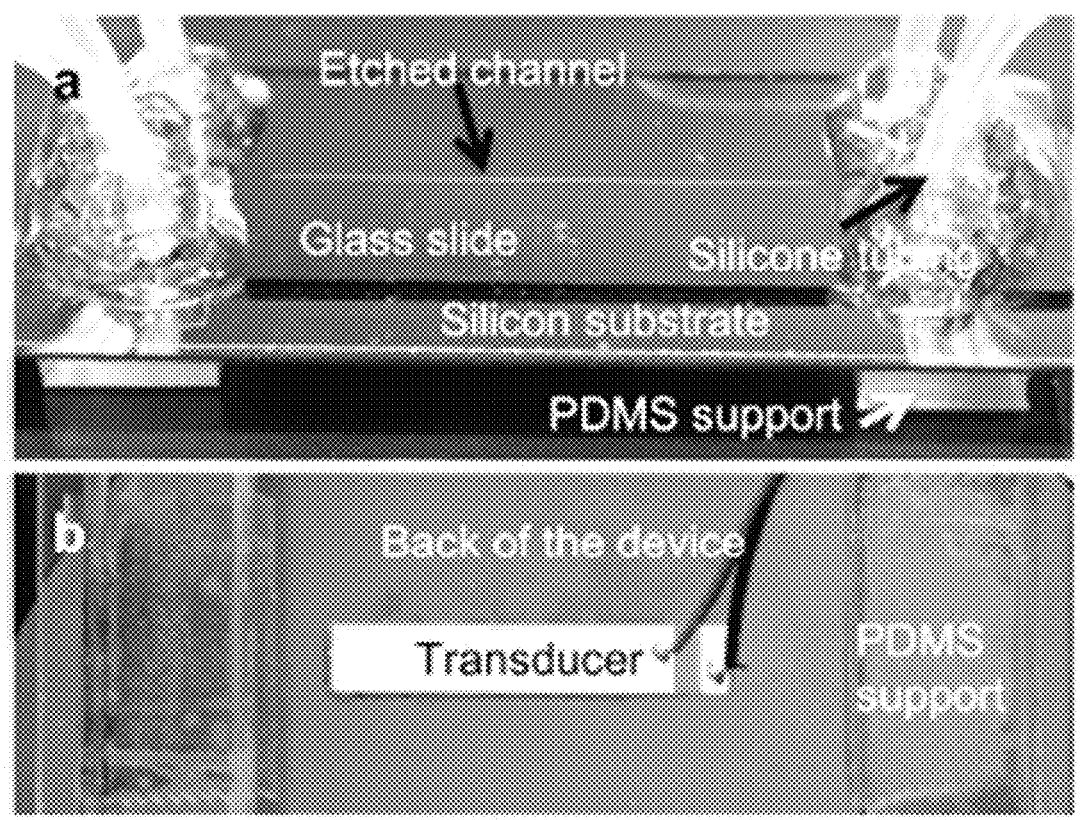
FIG. 4 PANEL A shows a top view of the microfluidic device with three silicone tubing inlets and outlets.

A silicon-glass microfluidic device consisting of one main channel with trifurcated inlets and outlets was constructed. A 100 mm silicon wafer was photo-patterned with positive photoresist and etched via deep reactive ion etching. A borosilicate glass slide was anodically bonded to the top surface of the etched wafer. Silicon tubing was used for the liquid connection. FIG. 4 PANEL A shows a top view of the microfluidic device with three silicone tubing inlets and outlets. The microchannel is enclosed with an anodically bonded class side and silicone tubing-PDMS slab is plasma sealed to the slide.

A piezoelectric transducer (l=3 cm, w=0.5 cm) with a resonance frequency of 2.91 MHz was superglued to the bottom of the channel in the longitudinal direction to generate standing acoustic waves. The assembled device was mounted on a glass slide using PDMS slabs as supports and double-sided tape as an adhesive. FIG. 4 PANEL B shows the bottom view of the microfluidic device with the attached transducer and the PDMS supports.

Figure 5:
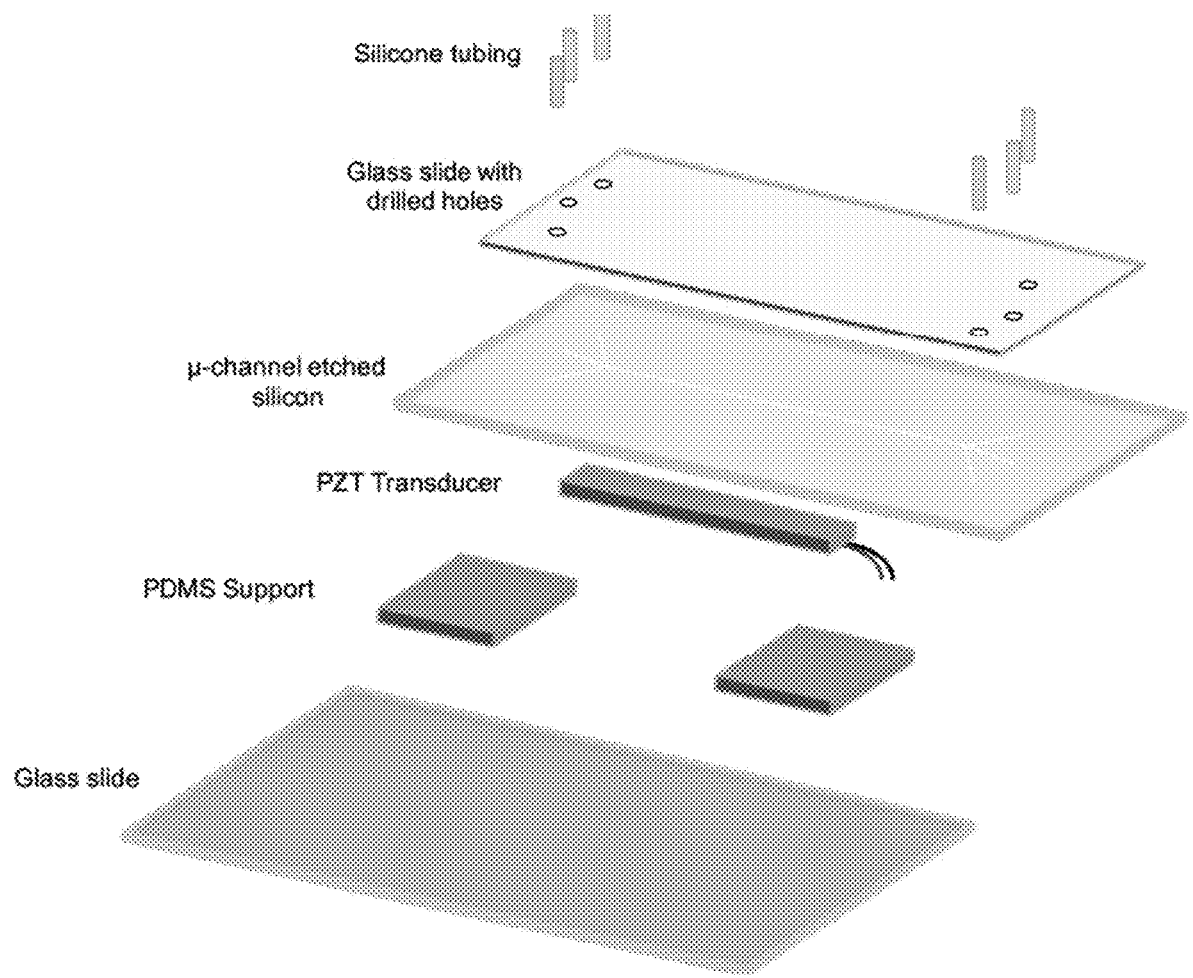
FIG. 5 illustrates the assembly of components to build the microfluidic device.

FIG. 5 illustrates the assembly of an example microfluidic device. A glass slide is used as a base, and a PZT transducer is placed between two PDMS support pieces. A μ-channel etched silicon wafer is placed on top of the PZT transducer and PDMS supports. A glass slide with drilled holes is prepared and placed on top of the μ-channel etched silicon wafer. Silicon tubing is connected to the drilled holes of the glass slide.

Figure 6:
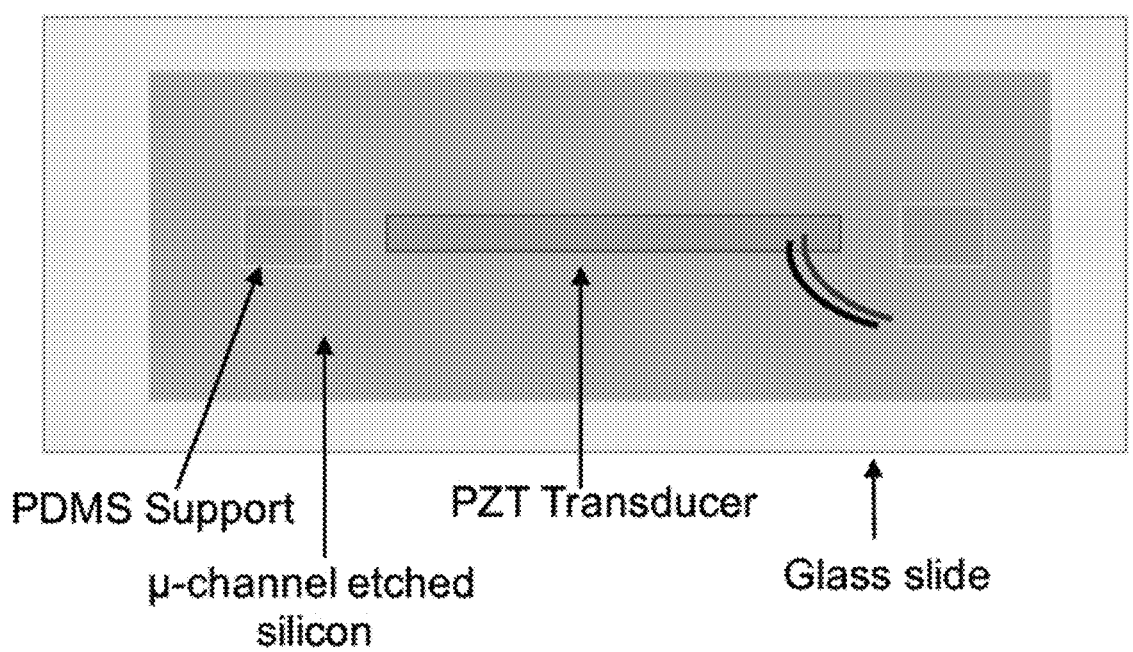
FIG. 6 illustrates a bottom view of a microfluidic device.
Figure 7:
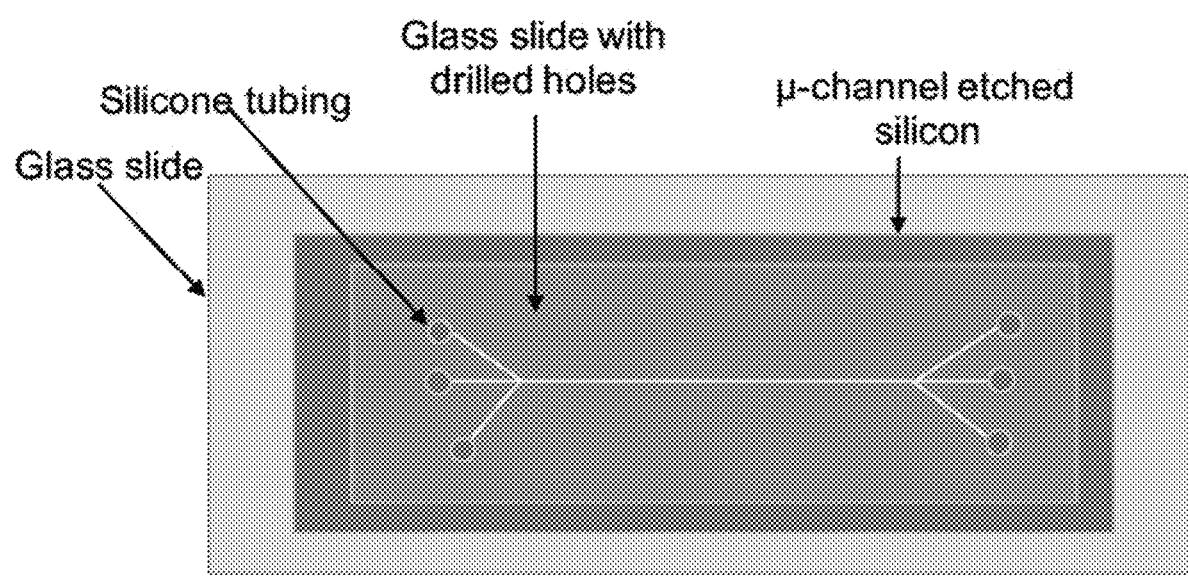
FIG. 7 illustrates a top view of a microfluidic device.
Figure 8:
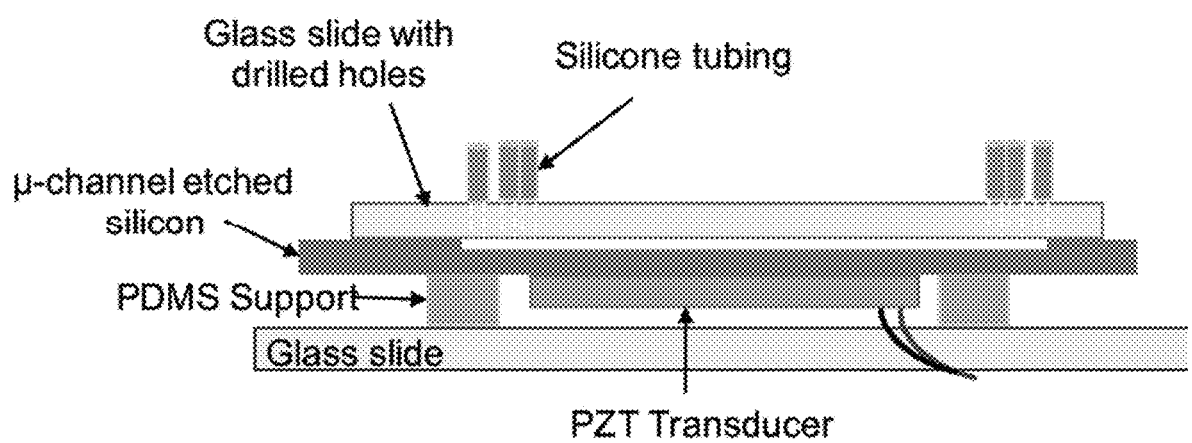
FIG. 8 illustrates a side view of a microfluidic device.
Figure 9:
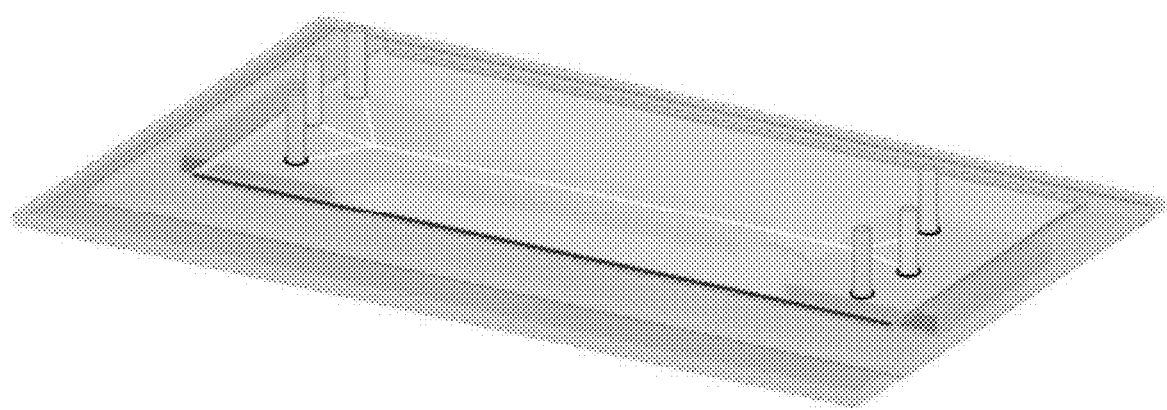
FIG. 9 illustrates a fully assembled microfluidic device.

FIG. 6 illustrates the bottom view of a microfluidic device. The PZT transducer is placed between two PDMS support pieces. FIG. 7 illustrates a top view of a microfluidic device. A glass slide with drilled holes is placed on top of a μ-channel etched silicon wafer, and silicon tubing is used to provide access to the etched channels. FIG. 8 illustrates a side view of a microfluidic device. FIG. 9 illustrates a fully assembled microfluidic device.

Example 4: Sample Preparation

Fluorescent and non-fluorescent solutions with different mass densities, solutions containing mixtures of suspended microparticles and sub-microparticles, *E. coli*, and B-RBCs were prepared. 2.5 μM fluorescein solutions were prepared by dissolving fluorescein sodium salt in de-ionized water and in 0.1×PBS buffer. For particle mixtures, fluorescent non-ribosomal peptide synthetase (NRPS) with different diameters were suspended in de-ionized water. B-RBCs and *E. coli* were diluted in 1×PBS buffer.

Example 5: Optimization of the Device for Fluid Relocation

The optimum resonance frequency of the microfluidic device that facilitates fluid relocation was determined using two density mismatched aqueous solutions: de-ionized water stained with 2.5 μM fluorescein, and 1×PBS buffer (100 mM NaCl and 2.7 mM KCl). The buffer solution was introduced as two lateral streams at flow rates of 75 μL/min. The fluorescein-stained de-ionized water was introduced as the central stream at a flow rate of 25 μL/min. The fluid flow patterns were monitored via an epi-fluorescence microscope.

Figure 10:
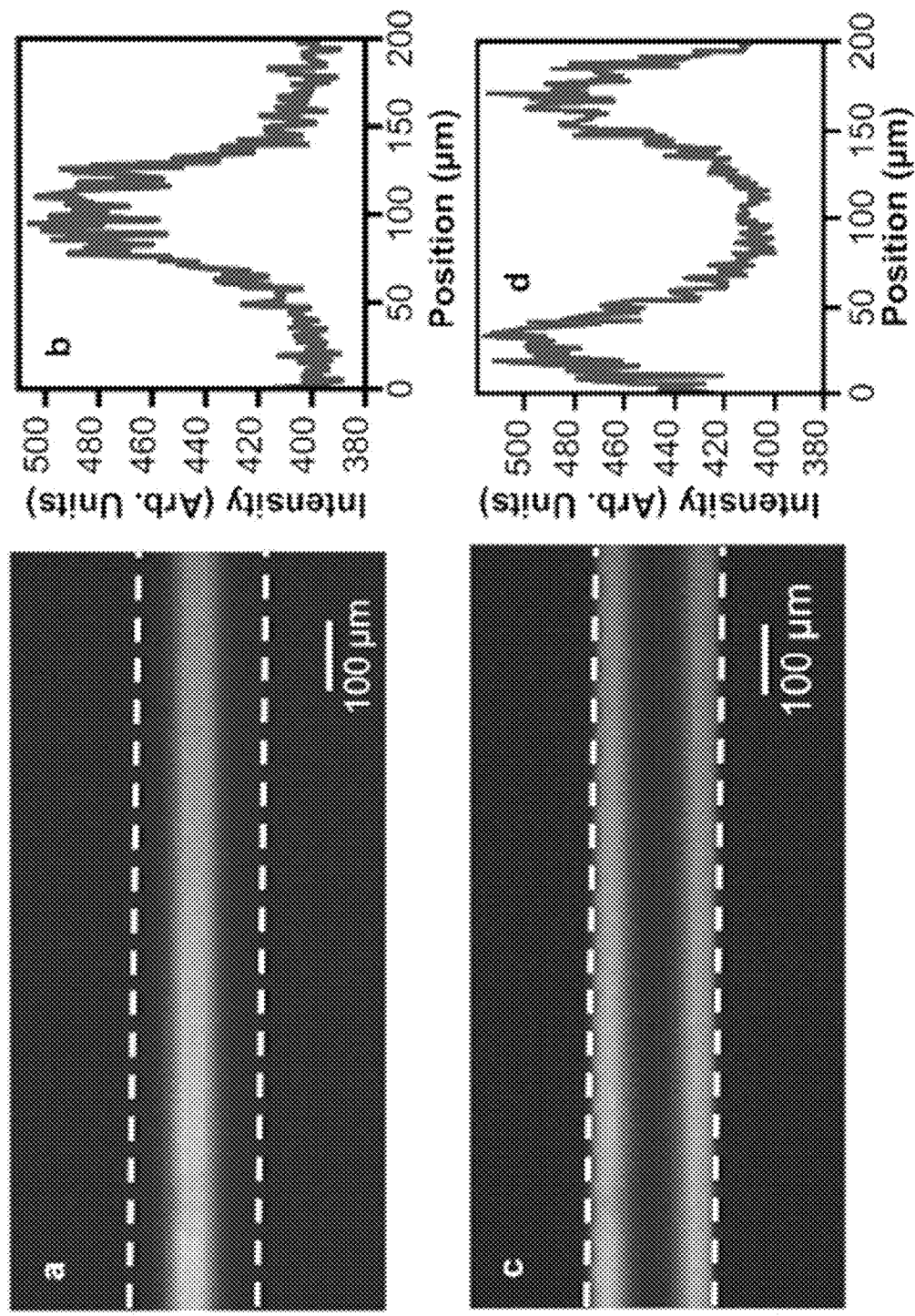
FIG. 10 PANEL A shows the laminar flow of three streams in the absence of an acoustic force.

The laminar flow conditions of the device made the three streams flow parallel to each other with a negligible amount of diffusive mixing at each flow interface. FIG. 10 PANEL A shows the laminar flow of three streams in the absence of an acoustic force. The two lateral streams were 1×PBS, and the central stream was 2.5 μM fluorescein in de-ionized water. The acoustic frequency of the device was scanned from 2.5 MHz to 3.5 MHz, and the applied voltage (Vpp) was kept constant at 20.0 Vpp. Maximum fluid relocation occurred at 3.31 MHz.

Once the effective resonance frequency was established, the applied voltage was scanned from 2 Vpp to 20 Vpp to find the lowest possible applied voltage that could generate fluid relocation. Stable fluid relocation occurred at 10.8 Vpp. The width of each fluid stream was maintained by controlling relative fluid flow rates using syringe pumps. The width of each 1×PBS stream was maintained around 50 μm, and the width of the de-ionized water stream was maintained at about 100 μm. FIG. 10 PANEL B shows the flow profiles of the 1×PBS solution and the 2.5 μM fluorescein solution.

During fluid relocation, the two lateral IX PBS streams were relocated and combined at the center of the channel. FIG. 10 PANEL C shows the relocation of the 1×PBS and 2.5 μM fluorescein solution in the presence of an acoustic wave field. The fluorescein-stained water stream in the center was split and relocated into two lateral positions of the channel. Each of lateral stream was about 50 μm wide, and the new central stream was about 100 μm wide. FIG. 10 PANEL D shows the flow profiles of the relocated streams.

The data indicated that the initial relative widths could be maintained once the fluid streams were established. The epi-fluorescence images (FIG. 10 PANEL A and PANEL C) indicate the absence of sharp fluid boundaries between the PBS and de-ionized water streams. Stream relocation was observed when the 1×PBS solution was replaced with a 0.1×PBS solution. The ten-fold dilution of the buffer solution had no visible impact on the extent and or speed of stream relocation. The data demonstrated that the denser solution must initially be at the lateral position for relocation to occur.

Fluorescein was used to visualize the different flow paths. When the experiment was repeated with a 2.5 μM fluorescein solution in water as the two lateral streams and pure de-ionized water as the central stream, fluid relocation was not observed, indicating that the use of 2.5 μM fluorescein did not affect flow relocation. Flow rates of up to 500 μL/min were tested, and a loss of fluid relocation was not observed.

Example 6: Particle Manipulation and Separation

Experiments were conducted with aqueous suspensions comprising 0.25 μm, 0.53 μm, and 0.84 μm diameter particles. The particle concentration of each suspension was maintained at about 50000-100000 particles/mL. Each sub-microsphere suspension was introduced to the channel via the central inlet at a flow rate of 50 μL/min. Particle-free 1×PBS was introduced via the two lateral inlets at a flow rate of 75 μL/min.

To investigate the separation of sub-micron sized particles from micron sized particles, a binary mixture of microspheres and sub-microspheres suspended in de-ionized water was introduced from the central inlet, and 1×PBS buffer was introduced from two lateral inlets. The composition of both particle types was maintained to be equal as possible. For biological samples, a mixture of B-RBCs and *E. coli* in 1×PBS (low density buffer) was introduced via the central inlet, and a 1×PBS solution containing 0.2 M NaCl (high density buffer) was introduced via two lateral inlets. The resonance standing acoustic waves were generated using a waveform generator and amplified using an RF amplifier. The acoustic performance parameters (i.e., frequency, applied voltage, amplitude) were monitored using an oscilloscope.

Example 7: Fluorescence Imaging and Flow Cytometry Analysis

To evaluate the flow relocation and particle separation, fluorescence images and video clips of fluid and particle streams in the microfluidic channel above the PZT or near the trifurcated outlet were captured using an epi-fluorescence microscope equipped with an sCMOS camera. The flow profile of a sample was obtained by line scanning the image across the channel. A FACSCalibur™ flow cytometer was used to analyze samples collected from each outlet before and after the fluid relocation.

The composition of NRPS particles and cells in a sample was determined using flow cytometry dot plots. Pure samples of NRPS particles and cells were first measured to define the regions of interest in each dot plot and to set the gates accordingly for each particle or cell type. The defined regions were used to identify and calculate the percentage composition of particles or cells present in a particular mixture. NRPS particle populations were gated based on a population's fluorescence intensity via the fluorescence intensity (FL2) fluorescence channel of the flow cytometer, which detected fluorescence at 585±21 nm and side scattering. The data were presented in the form of dot plots of side scatter (SSC) vs. FL2.

Mixtures of non-labeled cells (*E. coli* and B-RBCs) were analyzed using size differences, and are presented as dot plots of SSC vs. forward scatter (FSC) plots. All data collection and analysis were performed using CellQuest™ Pro and FCS Express 5 software, respectively. A total of 10,000 events were measured in each measurement, and the instrument threshold was set at FL2 and/or SSC to remove unwanted events resulting from non-fluorescent particles and/or debris. An internal calibration method was employed using flow cytometry standard beads to determine the particle concentration of samples. One milliliter of a bead sample was mixed with 50 µL of standard CountBright™ absolute counting beads. The concentration of particles was calculated using the following equation:

$$\text{Concentration (per mL)} = \left(\frac{\text{\# of particle events}}{\text{\# of standard bead events}}\right)\left(\frac{\text{Standard beads in total volume}}{\text{Total volume (mL)}}\right)$$

Example 8: Fluid Relocation Study

Two fluid streams with mismatched densities were acoustically relocated in a microfluidic channel while being flowed parallel to each other. First, a 1×PBS solution was introduced as two lateral streams, and de-ionized water was introduced as the central stream. The laminar flow condition made these three streams flow parallel to one another with negligible mixing at the interfaces.

Figure 11:
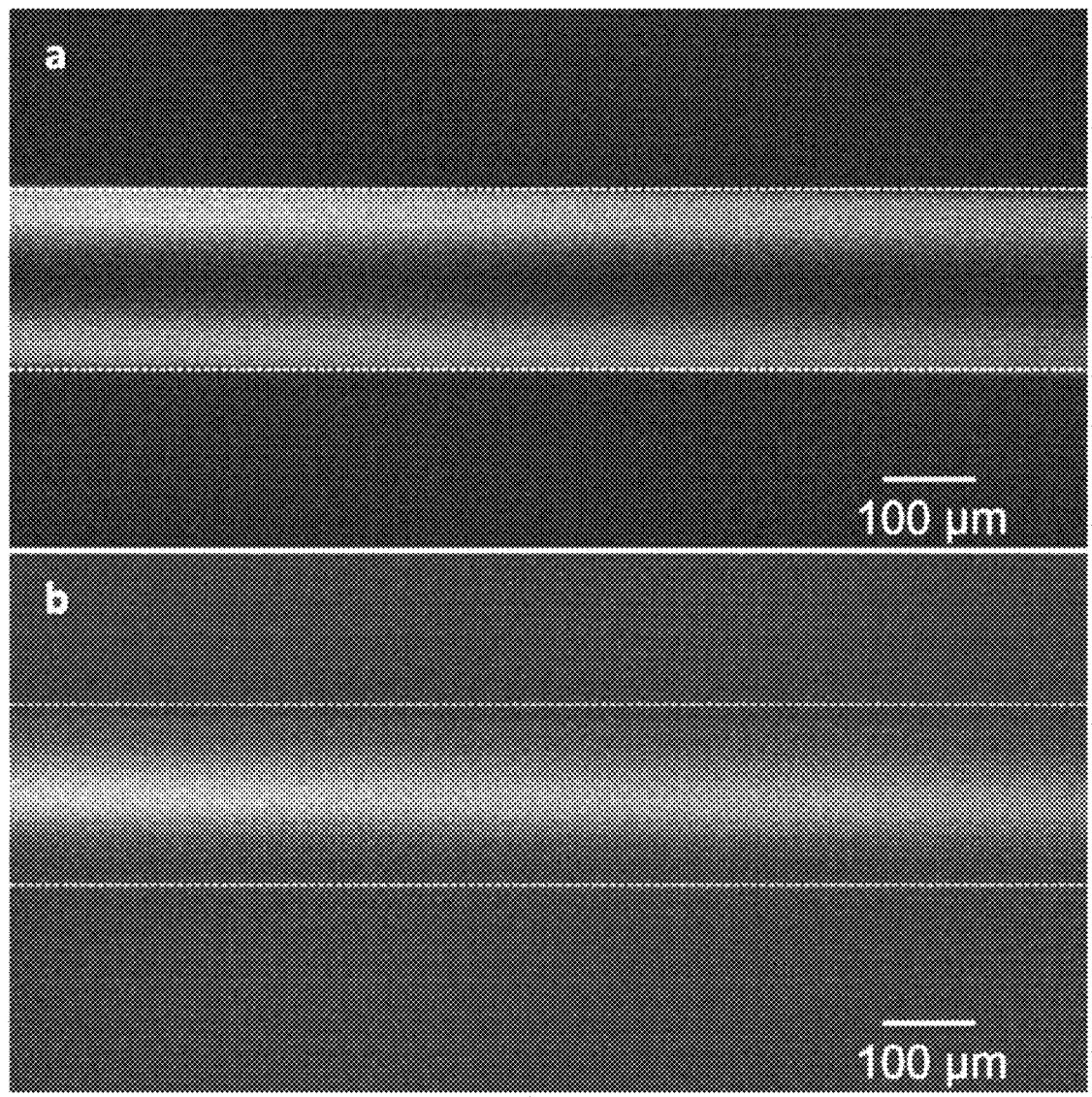
FIG. 11 PANEL A shows fluorescence micrographs of the two lateral streams of a 2.5 μM fluorescein solution in 1×PBS before an acoustic field is applied. The de-ionized water stream is flowing in the middle.

FIG. 11 PANEL A shows fluorescence micrographs of the two lateral streams of a 2.5 µM fluorescein solution in 1×PBS before an acoustic field was applied. The de-ionized water stream is flowing in the middle.

When an acoustic field was applied at 3.31 MHz with an applied peak-to-peak voltage ($V_{pp}$) of 75 my, the 1×PBS streams moved to the center of the channel, and the de-ionized water stream was split and relocated as two lateral streams. The relative flow rates controlled the width of each stream. The width of the PBS central stream was the same as the width of the central outlet (100 µm); each PBS stream prior to relocation was maintained at a width of 50 µm or less. When the IX PBS solution was replaced with 0.1×PBS, the stream relocation occurred as usual. The one-fold dilution of PBS had no observed effect on the extent and speed of fluid stream relocation.

FIG. 11 PANEL B shows the switching of streams upon application of an acoustic field.

Fluid relocation occurred only when the denser PBS solution was placed in the lateral streams. When the experiment was repeated with a 2.5 µM aqueous fluorescein solution as the two lateral streams and pure de-ionized water as the central stream, flow switching was not observed. The result indicated that little or no effect from the 2.5 µM fluorescein on flow switching. However, higher fluorescein concentrations can generate flow switching because the density of the medium increases as the concentration of fluorescein increases. Total flow rates of up to 400 µL/min were tested without any effect on fluid relocation.

Figure 12:
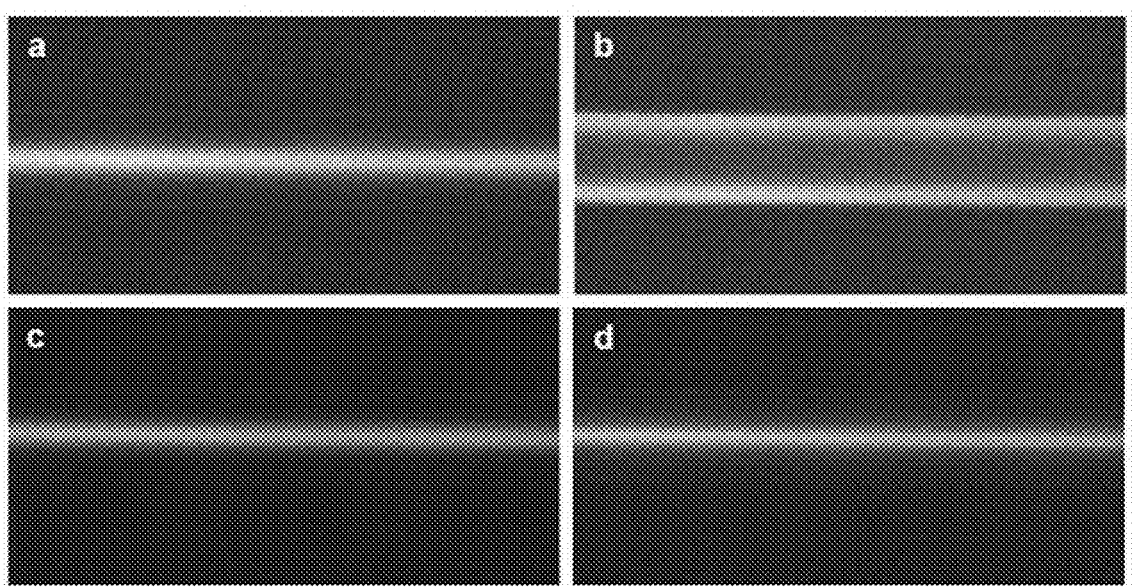
FIG. 12 PANEL A shows an epi-fluorescence micrograph of a laminar flow of 0.1×PBS (lateral) and 2.5 µM fluorescein in de-ionized water (central) stream in the absence of an acoustic force.

FIG. 12 PANEL A-FIG. 12 PANEL D shows epi-fluorescence micrographs showing the density dependence of fluid relocation. FIG. 12 PANEL A shows an epi-fluorescence micrograph of a laminar flow of 0.1×PBS (lateral) and 2.5 µM fluorescein in de-ionized water (central) stream in the absence of an acoustic force. FIG. 12 PANEL B shows an epi-fluorescence micrograph showing the relocation of lateral 0.1×PBS streams and a 2.5 µM fluorescein stream upon application of an acoustic force. FIG. 12 PANEL C shows an epi-fluorescence micrograph of the laminar flow of three streams of 2.5 µM fluorescein in de-ionized water as the central stream, and de-ionized water as the lateral streams in the absence of an acoustic force. FIG. 12 PANEL D shows an epi-fluorescence micrograph showing that there was no relocation of the 2.5 µM fluorescein solution and de-ionized water streams upon applying an acoustic force.

Example 9: Separation of Nanoparticles

To demonstrate the separation of nanoparticles, a binary mixture of 90 nm Nile red particles and 2 µm yellow fluorescent particles suspended in de-ionized water was introduced into the channel via the middle inlet. PBS buffer with 2.5 µM fluorescein was introduced via the two lateral inlets. Fluorescein was used to monitor the movement of the flow streams.

In another experiment, a mixture of lipid vesicles with diameters of 300 nm or below and 3 µm polystyrene particles was used. Lipid vesicles were prepared using a 100:1 molar mixture of 1,2-dimyristoyl-sn-glycero-3-phosphorylcholine (DMPC) and N-(fluorescein-5-thiocarbamoyl)-1,2-dihexadecanoyl-sn-glycero-3-phosphoethanolamine (DHPE) fluorescent lipid via an extrusion method.

Figure 13:
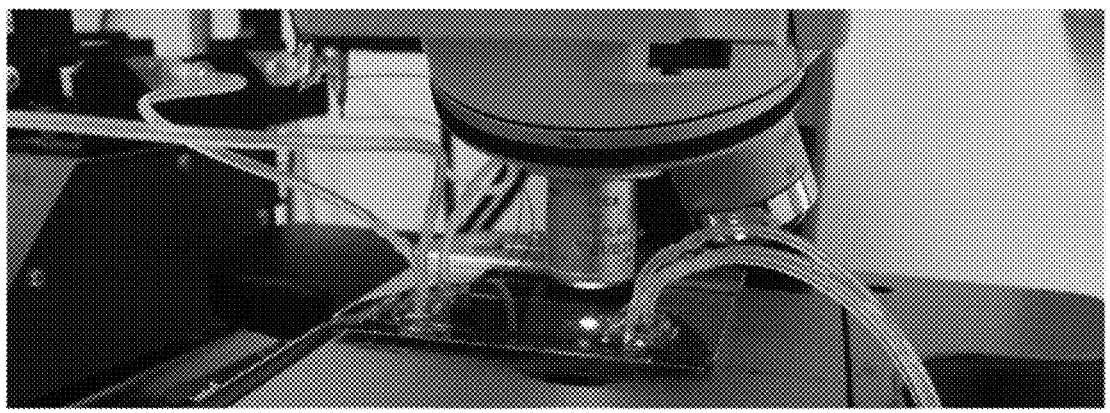
FIG. 13 shows the epi-fluorescence microscope set up that was used to collect fluorescence data.

Resonance standing acoustic waves were generated using a waveform generator. The acoustic waves were amplified via an RF amplifier. The acoustic performance parameters (i.e., frequency, applied voltage, amplitude) were monitored using an oscilloscope. Fluorescence images of fluid streams and particles were collected using an epi-fluorescence microscope equipped with an sCMOS camera. FIG. 13 shows the epi-fluorescence microscope set-up that was used to collect fluorescence data.

Example 10: Relocation of Sub-Micron Particles

Figure 14:
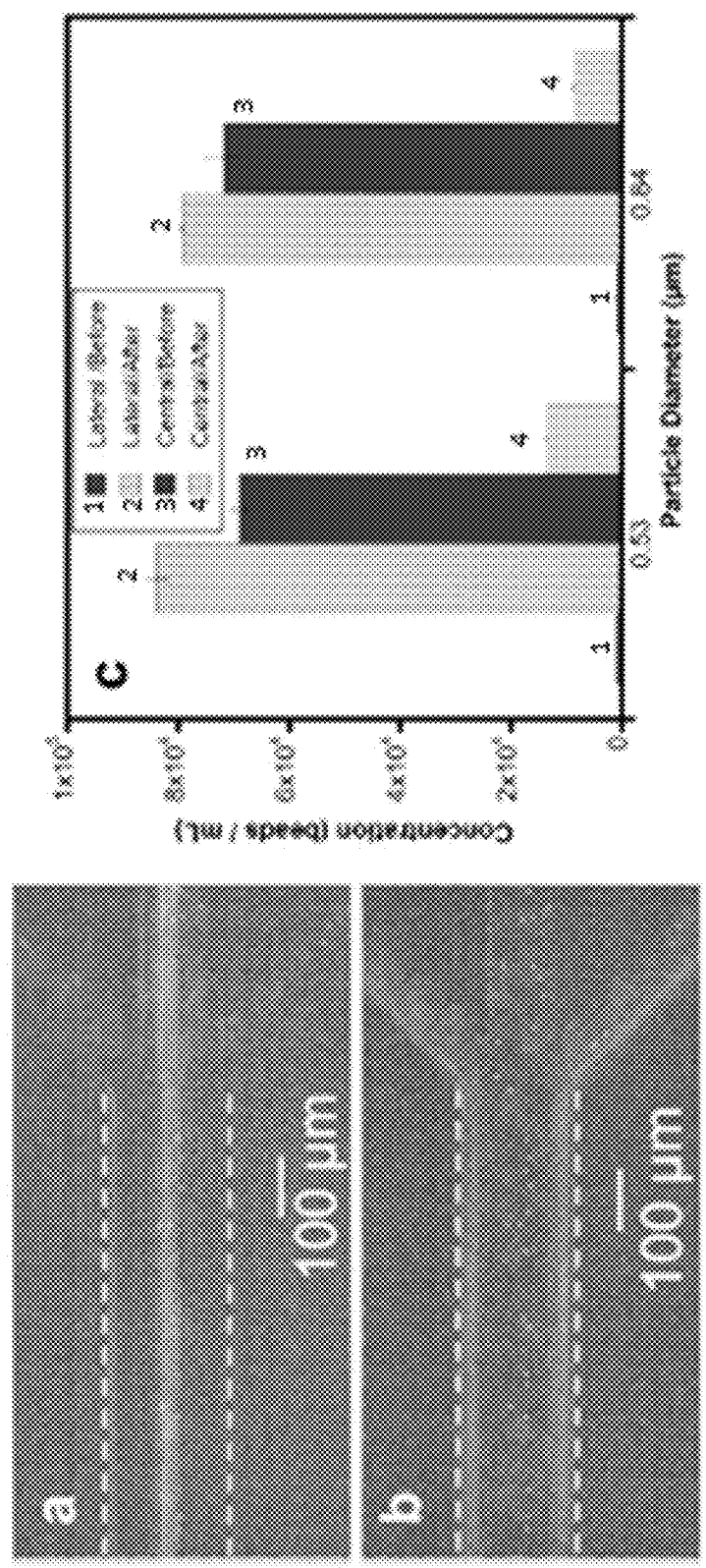
FIG. 14 PANEL A shows the epi-fluorescence micrograph of the 0.53 µm particles in the central stream.

Sub-micron sized particles were separated from micron-sized particles using acoustophoresis in combination with fluid relocation. The relocation of individual sub-micron particles was determined using NRPS particles with diameters of 0.25 µm, 0.53 µm, and 0.84 µm. The sub-micron particles of a specific size were suspended in de-ionized water, and introduced to the microfluidic device via the central inlet at a flow rate of 50 µL/min. A 1×PBS solution was introduced to the microfluidic device via two lateral inlets at a flow rate of 75 µL/min. FIG. 14 PANEL A shows the epi-fluorescence micrograph of the 0.53 µm particles in the central stream.

Complete relocation of the sub-micron particles to the lateral stream was observed at an acoustic standing wave field of 3.30 MHz and applied voltage of 12 Vpp. FIG. 14 PANEL B shows the relocation of the sub-micron particles to the lateral stream. The small dots in the middle of the channel are a small fraction of particles that were adhered to the surface of the channel. The adhered particles did not impact the fluid relocation of the sub-micron particles.

The extent of relocation of the sub-micron particles was determined via flow cytometry measurements of the particle streams collected from each outlet before and during the fluid relocation process. Only the 0.53 µm and 0.84 µm particles were relocated. The fluorescence intensity of the 0.25 µm particles was not high enough to produce visible epi-fluorescence images.

Flow cytometry analysis showed that the two lateral streams contained a small amount of particles prior to fluid relocation. Sample loss resulting from diffusion and the random movement of particles was about 1000 particles/mL for the 0.53 µm particles, and was negligible compared to the total particle concentration. The total average concentration of particles in the two lateral streams increased to about 84,000 particles/mL during fluid relocation. The 84-fold increase in particle concentration demonstrated that sub-micron particles can be efficiently manipulated using drag forces of a relocating fluid, while keeping sample loss resulting from diffusion minimal.

The concentration of particles in the original central particle stream decreased by about 80% during the relocation process. For the 0.84 µm particles, the average concentration of particles in the two lateral streams was about 800 particles/mL. The average concentration of particles in the two lateral streams increased to about 80,000 particles/mL during fluid relocation. The concentration of the 0.84 µm particles was enhanced by 100-fold, and the concentration of particles in the original central particle stream decreased by about 88% during fluid relocation. FIG. 13 PANEL C shows the concentration of sub-micron particles in the lateral and central streams before and after fluid relocation.

Example 11: Separation of Nanoparticles from Microparticles

Figure 15:
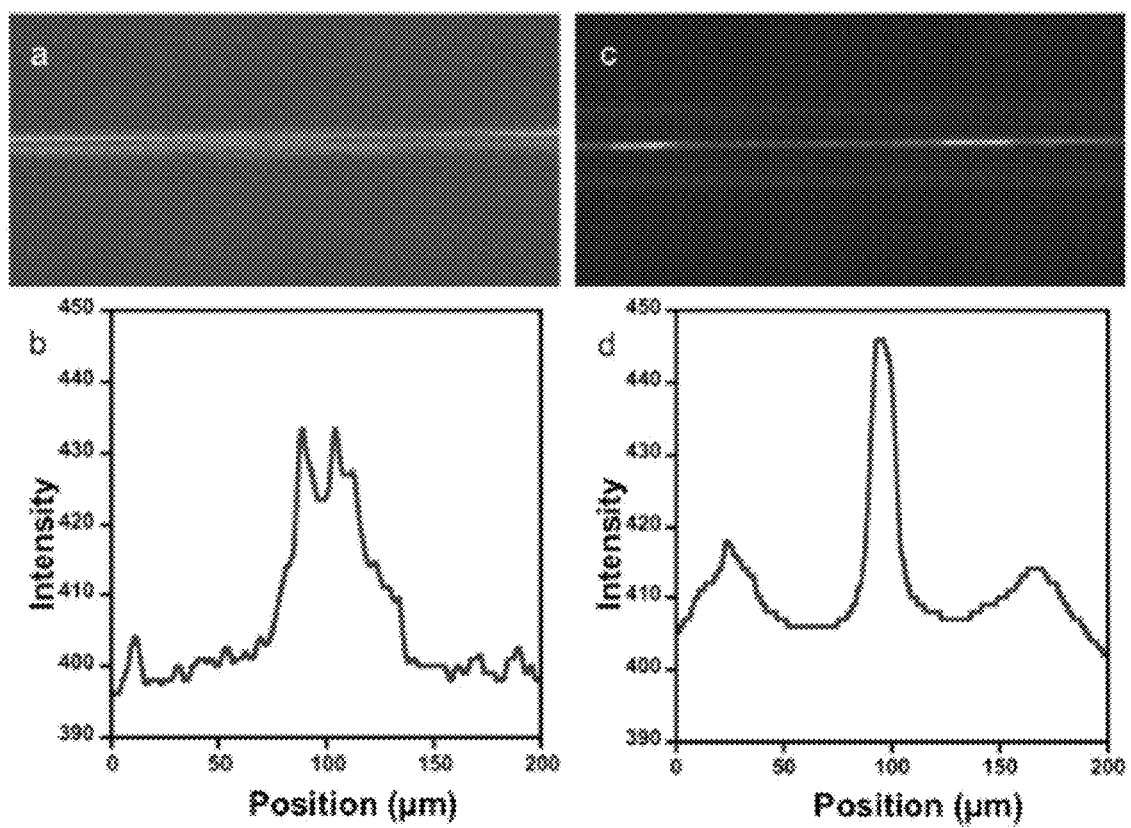
FIG. 15 PANEL A is a fluorescence micrograph that shows the mixture of nanoparticles and microparticles in the central stream.

A solution containing nanoparticles and microparticles in water was introduced via the central inlet, and a 0.1×PBS solution was introduced via the two lateral inlets. 100 nm polystyrene particles were used as nanoparticles, and 2 µm polystyrene particles were used as microparticles. FIG. 15 PANEL A is a fluorescence micrograph that shows the mixture of nanoparticles and microparticles in the central stream.

FIG. 15 PANEL B shows a line scan analysis of the fluorescent flow stream profile, which was analyzed using Image software. The data indicated that the particles were initially dispersed at a width of about 60 µm along the center of the channel. The width of the central fluid stream was assumed to be about 60 µm, and the average width of each lateral stream was about 70 µm.

In the presence of resonance standing waves, the flow streams were relocated, and the 2 µm particles were acoustically focused toward the center of the microchannel. The primary acoustic forces on the nanoparticles were not strong enough to hold the nanoparticles along the center of the channel, and the nanoparticles were moved to the two lateral streams by the drag forces of the relocating fluid. The fluorescence intensities of the two lateral streams containing the nanoparticles were weaker than that of the central stream. This observation was mainly due to the smaller size of the nanoparticles. FIG. 15 PANEL C shows that in the presence of an acoustic field, the 100 nm nanoparticles were moved to the lateral stream while the 2 µm microparticles remained in the central stream.

FIG. 15 PANEL shows the background-corrected line scan profile of the fluorescence image, which shows the appearance of two fluorescence streaks from the flow of nanoparticles. The average width of each nanoparticle stream was about 58 µm, and the microparticles were focused to an average width of about 37 µm along the center of the channel. The sharp peak suggests that the microparticles were well focused at the center of the channel. The two broad and dim lateral peaks suggest that the nanoparticles were dispersed in the lateral streams. Equal splitting of the main channel into three outlets enabled the simultaneous separation of nanoparticles from the microparticles.

Example 12: Isolation of Nanometer-Sized Lipid Vesicles Suspended in De-Ionized Water Lipid vesicles were prepared via sonication and an extrusion method using 50 nm filters. The lipid vesicles were then suspended in DI water. The average diameter of the lipid vesicles obtained from dynamic light scattering measurements was about 200 nm. The lipid vesicle solution was introduced as the central stream. Upon applying a resonance frequency, the central stream was relocated as two lateral streams.

Figure 16:
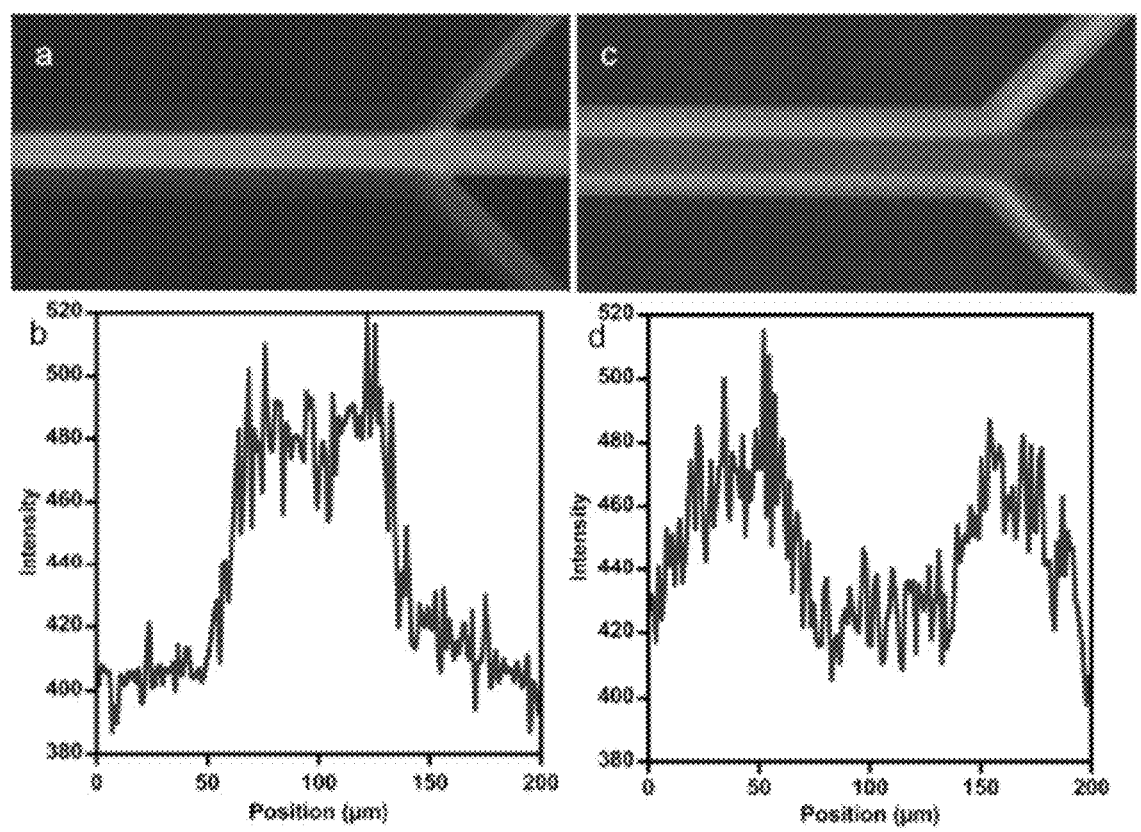
FIG. 16 PANEL A shows lipid vesicles with an average diameter of 200 nm in a main fluidic stream.

FIG. 16 PANEL A shows lipid vesicles with an average diameter of 200 nm in a main fluidic stream. FIG. 16 PANEL B shows the line scan image demonstrating the width of the central stream. FIG. 16 PANEL C shows lipid vesicles with an average diameter of 200 nm split into two lateral streams via acoustic fluid relocation. FIG. 16 PANEL shows the line scan image of the two lateral streams after acoustic fluid relocation.

Lipid vesicles are typically negative contrast particles that focus on the anti-pressure nodal planes of resonance standing waves. At an applied frequency of 3.31 MHz, the anti-pressure node was located near the two transverse walls of the microchannel. To monitor any acoustic focusing of the lipid vesicles in the absence of fluid relocation, a sample of the lipid vesicles suspended in de-ionized water was flowed through the central channel. Pure de-ionized water was flowed through the two lateral streams.

A small amount of lipid vesicles was acoustically focused to the anti-pressure nodes of the device in the presence of an acoustic field (FIG. 16 PANEL A). These vesicles were large enough to experience acoustic forces. The majority of the vesicles remained in the central stream. Although the average diameter of the vesicles was 200 nm, some vesicles were as large as a few micrometers in diameter. However, the majority of vesicles was not focused onto the anti-pressure node. This observation confirmed that most of the vesicles had diameters in the nanometer range.

Figure 17:
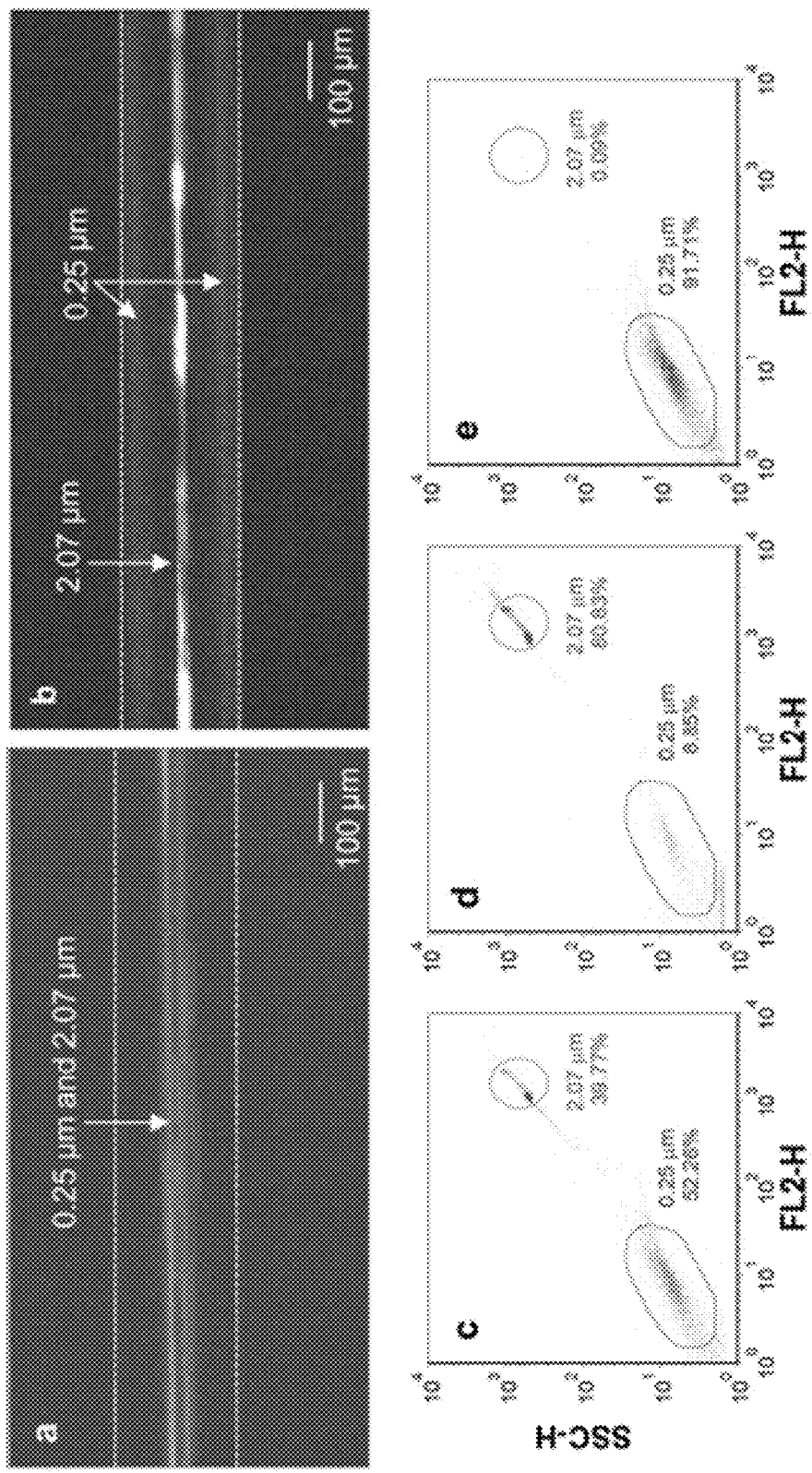
FIG. 17 PANEL A shows an epi-fluorescence micrograph of the mixture of 0.25 µm and 2.07 µm particles flowing in the central stream in the absence of an acoustic wave field.

Example 13: Separation of Micron-Sized Particles and Sub-Micron-Sized Particles The microfluidic device was used to isolate sub-micron sized particles from a binary mixture containing sub-micron sized particles and micron-sized particles. A mixture of 0.25 µm and 2.07 µm NRPS particles suspended in a low density fluid (i.e., de-ionized water) was introduced from the central outlet. FIG. 17 PANEL A shows an epi-fluorescence micrograph of the mixture of 0.25 µm and 2.07 µm particles flowing in the central stream in the absence of an acoustic wave field. In the presence of an acoustic standing wave field, the micron-sized particles were focused and remained in the central stream. The 0.25 µm particles were dragged with the low density fluid and were relocated to the lateral streams. FIG. 17 PANEL B shows an epi-fluorescence micrograph, where the 0.25 µm particles are dragged to the lateral stream along with the fluid, and the 2.07 µm particles are focused to the central stream in the presence of an acoustic wave field.

Scatter dot plots of side scatter vs fluorescence emission were used to calculate the percentages of the NRPS population in each sample. FIG. 17 PANEL C shows the flow cytometry scatter dot plot for the central stream with acoustics turned off. FIG. 17 PANEL D shows the flow cytometry scatter dot plot for the central stream with acoustics turned on. FIG. 17 PANEL E shows the flow cytometry scatter dot plot for the lateral stream with acoustics turned on. The central stream consisted of 52.26% 0.250 µm and 39.77% of 2.07 µm particles. During fluid relocation, the central stream was enriched with 2.07 µm particles, and the percentage of the 2.07 µm particles increased to 80.83%; the composition of the 0.25 µm particles decreased to 8.85%. The remaining population (about 10%) was considered to be debris in the sample. The two combined lateral streams consisted of 91.71% of the 0.25 µm particles and 0.09% of the 2.07 µm particles.

Figure 18:
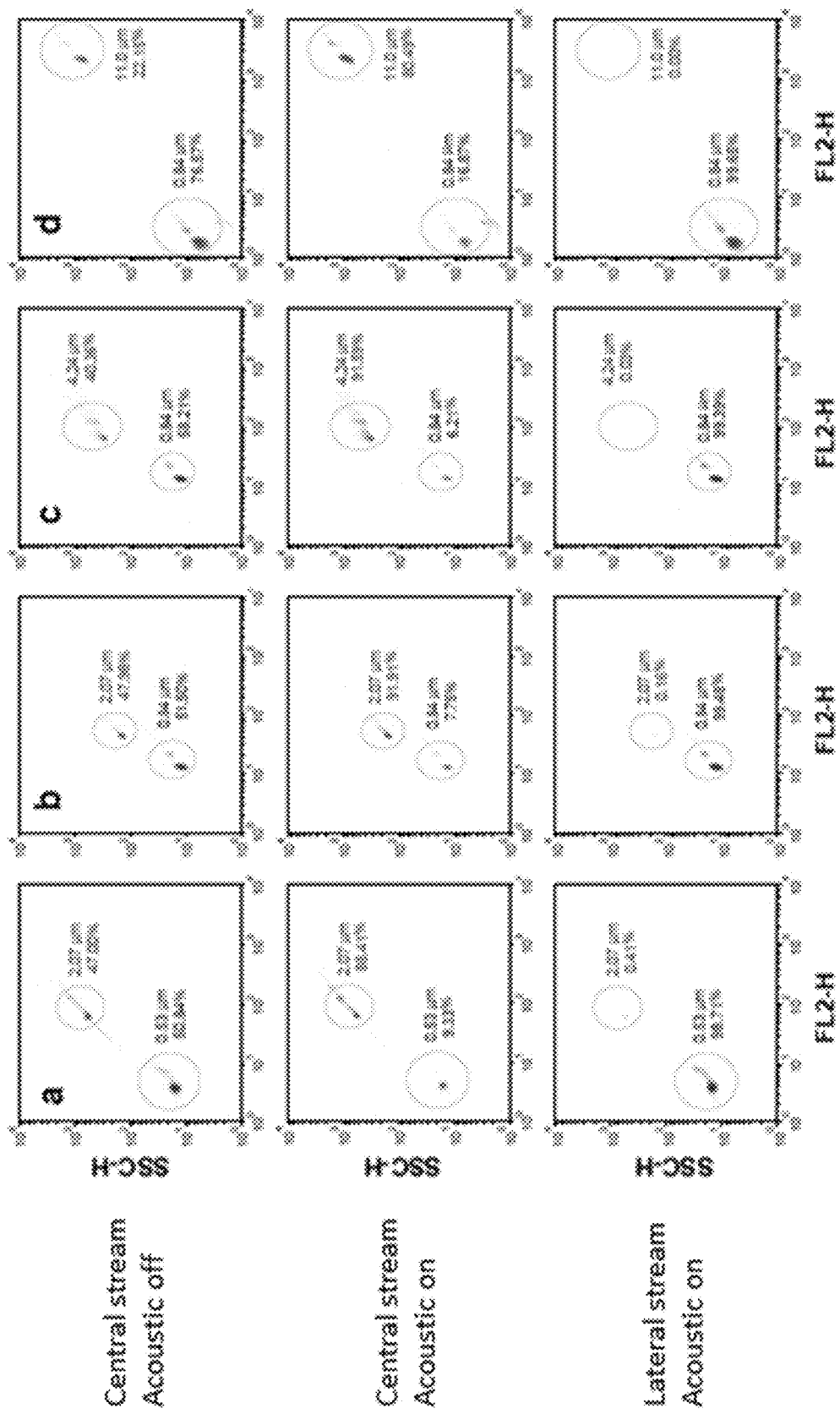
FIG. 18 PANEL A shows the separation of 2.07 µm and 0.53 µm particles.

Additional combinations of binary mixtures were also tested: mixtures of 0.53 µm and 2.07 µm particles, 0.84 µm and 2.07 µm particles, 0.84 µm and 4.24 µm particles, and 0.84 µm and 11.0 µm particles. FIG. 18 PANEL A-FIG. 18 PANEL D shows flow cytometry scatter plots demonstrating the separation of NRPS sub-micron-sized particles and micron-sized particles. FIG. 18 PANEL A shows the separation of 2.07 µm and 0.53 pin particles. FIG. 18 PANEL B shows the separation of 2.07 µm and 0.84 µm particles. FIG. 18 PANEL C shows the separation of 4.24 µm and 0.84 µm particles. FIG. 18 PANEL D shows the separation of 11.0 µm and 0.84 µm particles. The two gated regions indicate the percentages of particles.

The lateral stream was efficiently enriched with the sub-micron particles with percentages exceeding 90%. Particles that were smaller than 1 µm were relocated to the two lateral positions of the channel. The presence of a small fraction of smaller particles in the central stream (FIG. 11 PANEL D) during fluid relocation was attributed to diffusion and spillover of particles to the central stream. When the central stream was cycled through the device again, the central stream was completely enriched with micron sized particles.

Example 14: Separation of Micron-Sized Particles

Figure 19:
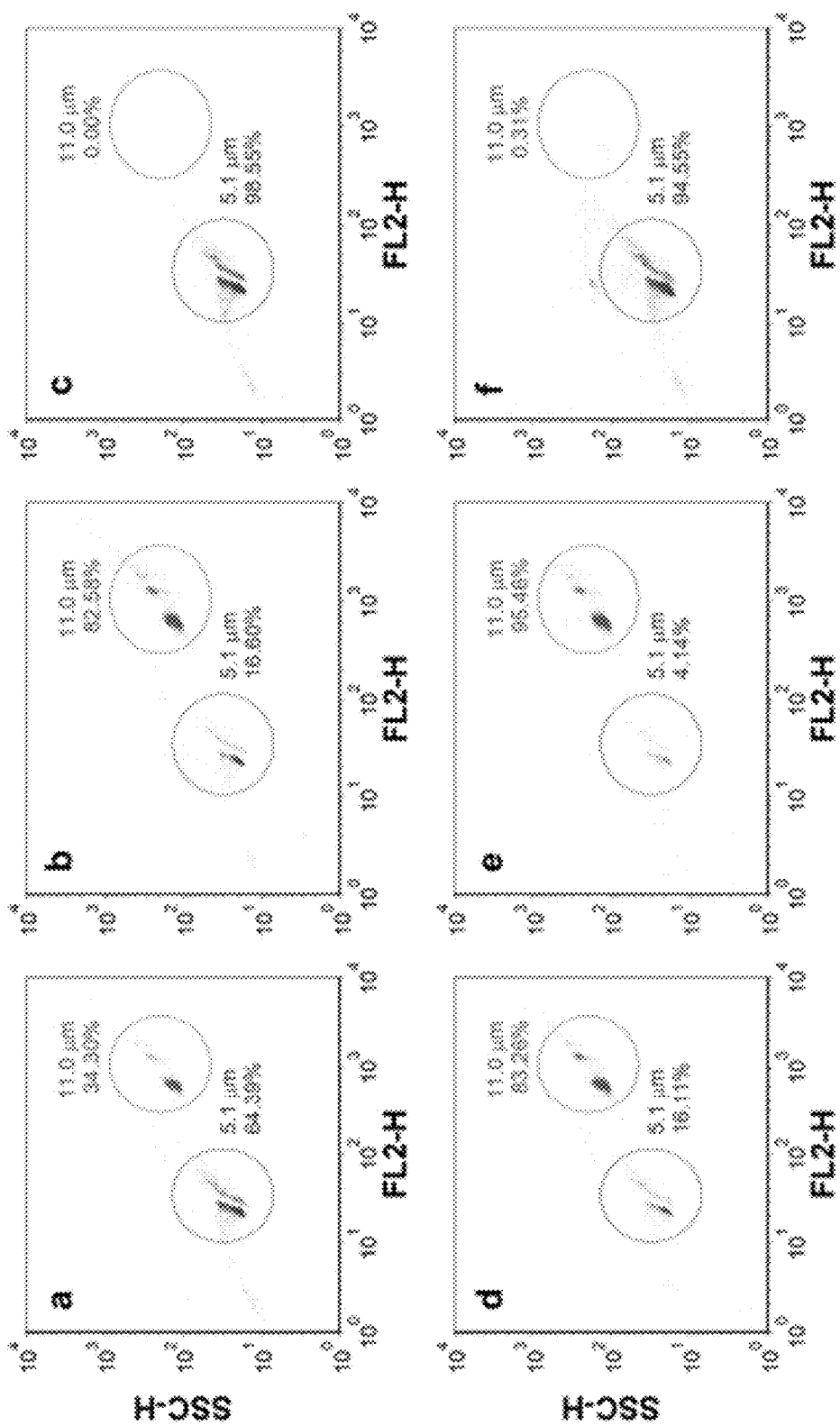
FIG. 19 PANEL A shows a flow cytometry scatter plot of the central stream in the absence of acoustics for the mixture containing 5.1 µm and 11.0 µm particles.

Two binary mixtures containing 5.1 µm and 11.0 µm particles, and 107 µm and 11.0 µm particles were used to test the ability of the microfluidic device to separate micron-sized particles. For the mixture containing 5.1 µm and 11.0 µm particles, the initial mixture contained 64.39% of the 5.1 µm particles and 34.30% of the 11 µm particles. FIG. 19 PANEL A shows a flow cytometry scatter plot of the central stream in the absence of acoustics for the mixture containing 5.1 µm and 11.0 µm particles. In the presence of acoustic focusing and fluid relocation, the central stream was enriched with 11.0 µm microspheres (82.58%). The central stream also contained 16.60% of the 5.1 µm particles. FIG. 19 PANEL B shows a flow cytometry scatter plot of the central stream in the presence of acoustics for the mixture containing 5.1 µm and 11.0 µm particles.

The lateral stream was fully enriched with the 5.1 µm microspheres (98.55%), and the 11.0 µm microspheres were not detected. FIG. 19 PANEL C shows a flow cytometry scatter plot of the lateral stream in the presence of acoustics for the mixture containing 5.1 µm and 11.0 µm particles. The flow cytometry analysis of the collected streams confirmed effective separation of microspheres of two sizes. Some of the 5.1 µm microspheres still remained in the central stream during the first relocation process. Further purification by recycling the central stream through the microfluidic device resulted in the central stream being enriched with 11.0 µm microspheres (95.46%) by relocating the remaining 5.1 µm particles to the lateral streams. FIG. 19 PANEL D shows a flow cytometry scatter plot of the central stream of a second run in the absence of acoustics. FIG. 19 PANEL E shows a flow cytometry scatter plot of the central stream of a second run in the presence of acoustics. FIG. 19 PANEL F shows a flow cytometry scatter plot of the lateral stream of a second run in the presence of acoustics. Similar outcomes were observed when subjecting a mixture of 2.07 µm and 11.0 µm particles to the microfluidics device.

Figure 20:
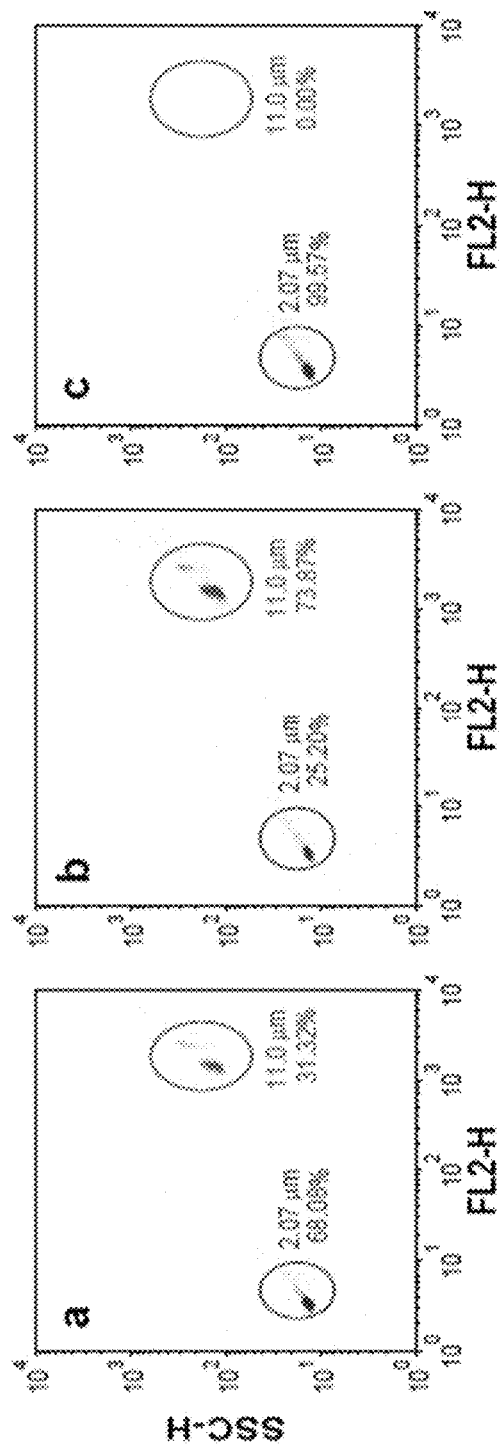
FIG. 20 PANEL A shows that the central stream had 68.08% of 2.07 µm particles and 31.32% of 11.0 µm in the absence of acoustics.

FIG. 20 PANEL A-FIG. 18 PANEL C shows scatter plots obtained from flow cytometry analysis showing separation of 11.0 µm and 2.07 µm Nile-red-stained polystyrene particles. FIG. 20 PANEL A shows that the central stream had 68.08% of 2.07 µm particles and 31.32% of 11.0 µm in the absence of acoustics. FIG. 20 PANEL B shows that the central stream had 25.20% of 2.07 µm particles and 73.87% of 11.0 µm in the presence of acoustics. FIG. 20 PANEL C shows that the lateral stream had 99.57% of 2.07 µm particles and 0.00% of 11.0 µm in the presence of acoustics. When acoustic focusing was turned on, large microspheres focused at the central stream, while the small microspheres relocated toward the lateral stream.

Binary mixtures containing of 6.43 µm and 11 µm particles; 3.42 µm and 6.43 µm particles; 4.24 µm and 6.43 µm particles; and 2.07 µm and 5.0 µm particles were also subjected to acoustic relocation, but separation was poor because the size difference between the two particle sizes were too close to obtain effective separation.

Example 15: Separation of *E. coli* and Bovine Red Blood Cells

To demonstrate the ability and efficiency of separation, and enrichment of small pathogenic microorganisms in blood samples using the microfluidic device, E. coli was separated from a pre-mixed sample containing E. coli and B-RBCs. E. coli and B-RBCs were distinguished based on the size difference using flow cytometry forward scatter plots. The relative positions of E. coli and B-RBs in cytometry scatter plots were first determined using unmixed samples of E. coli and B-RBCs.

Figure 21:
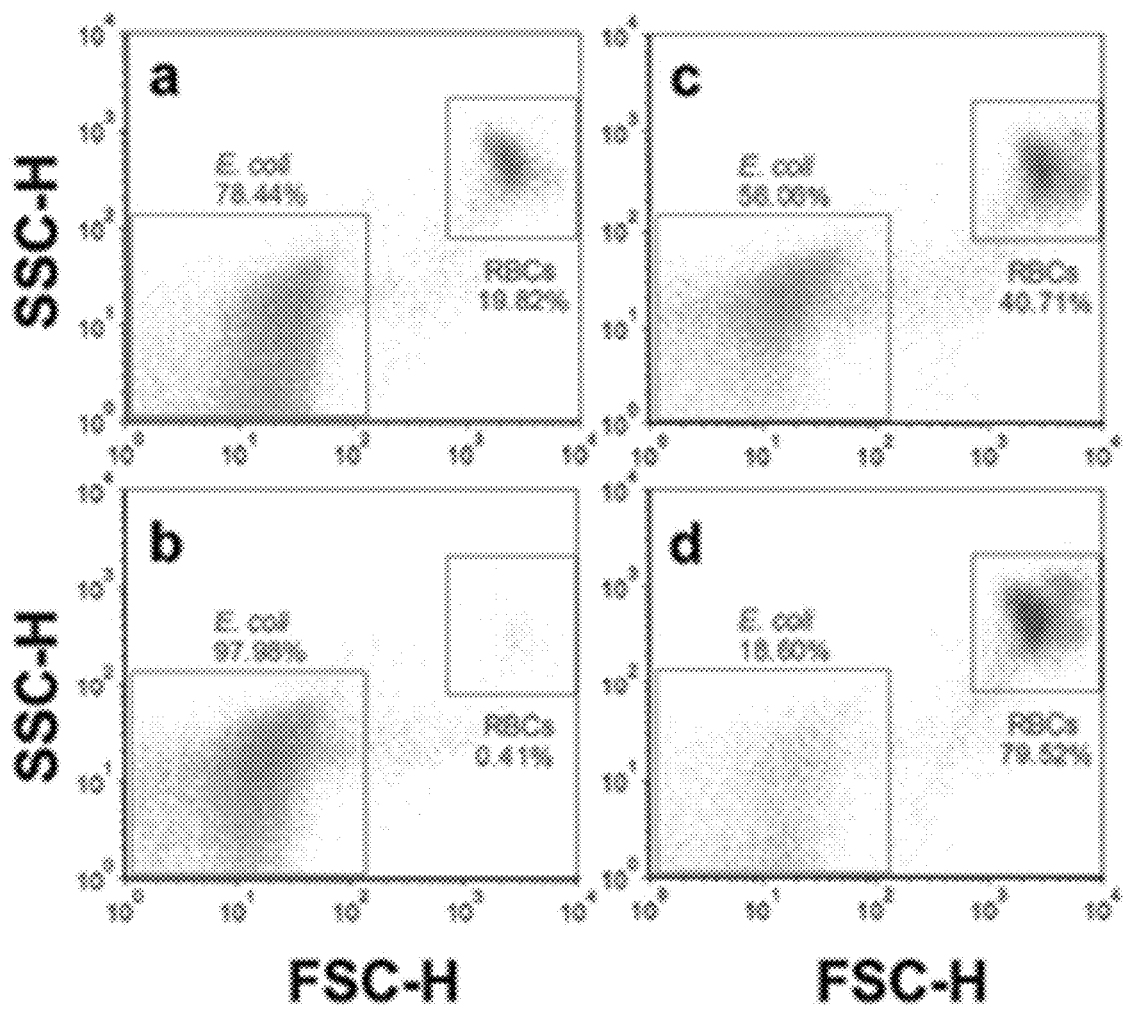
FIG. 21 PANEL A shows a flow cytometry scatter plot of the lateral stream in the absence of acoustics.

The E. coli and B-RBC mixture was suspended in a low density PBS solution and introduced to the microfluidics device via the central inlet. The high density PBS solution was introduced to the microfluidics device via the lateral inlet. The percentage of E. coli in the initial mixture was 56.06%, and the percentage of the B-RBCs in the initial mixture was 40.71%. FIG. 21 PANEL A shows a flow cytometry scatter plot of the lateral stream in the absence of acoustics. FIG. 21 PANEL C shows a flow cytometry scatter plot of the central stream in the absence of acoustics.

During fluid relocation, E. coli relocated to the lateral stream. The composition of the lateral stream was 97.98% E. coli. FIG. 21 PANEL B shows a flow cytometry scatter plot of the lateral stream in the presence of acoustics. The composition of the new central stream was 79.52% B-RBCs and 18.60% E. coli. FIG. 21 PANEL 1) shows a flow cytometry scatter plot of the central stream in the presence of acoustics. The central stream could be enriched further with B-RBCs by recycling the central stream through the microfluidics device.

Example 16: Comparison of Acoustophoresis and Acoustophoresis Combined with Acoustic Fluid Relocation for Micrometer Particle Separation The efficacy of acoustophoresis and acoustophoresis combined with acoustic fluid relocation in separating a binary mixture of micron sized particles was evaluated using a mixture containing of 5.1 μm and 11.0 μm particles. Sample solutions containing cells and/or particles suspended in a buffer or normal/de-ionized water were introduced to the microfluidic channels via the two lateral inlets. Clean buffer or water was introduced to the microfluidic channels via the central inlet. Syringe pumps were used to pump the fluids into the microchannel. Resonance standing waves were generated using the acoustic transducer that was attached to the bottom of the microchannel substrate. The acoustic forces created by the resonance standing waves focused the cells/particles to the center of the microchannel. The focused cells/particles were collected via the central outlet.

When using acoustophoresis alone the separate the particles, the 11 μm particles required a minimum resonance acoustic field 14.5 V. The flow rate for the lateral stream was 75 μL/min, and the flow rate for the central stream was 150 μL/min. Flow cytometry analysis showed that the percentage of the 11.0 μm particles was only 52.73%. At the minimum voltage, the fraction of the 5.1 μm particles was subjected to acoustophoresis, and the separation of the 5.1 μm and 11.0 μm particles was inefficient.

Figure 22:
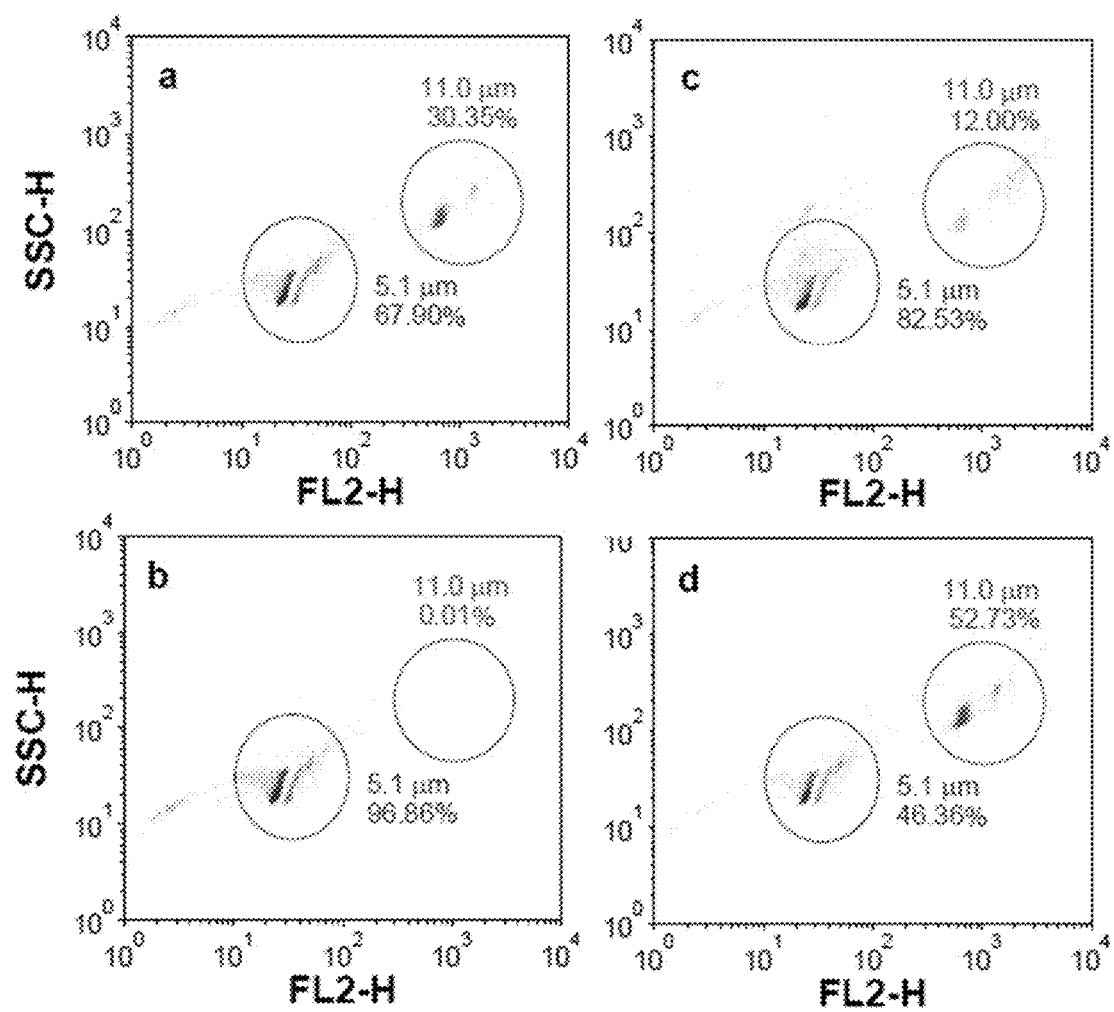
FIG. 22 PANEL A shows that the lateral stream had 67.90% of 5.1 µm particles and, 30.35% of 11.0 µm particles in the absence of acoustics.

FIG. 22 PANEL A-FIG. 22 PANEL D shows acoustophoresis of a binary mixture with 5.1 μm and 11.0 μm particles. FIG. 22 PANEL A shows that the lateral stream had 67.90% of 5.1 μm particles and 30.35% of 11.0 μm particles in the absence of acoustics. FIG. 22 PANEL B shows that the lateral stream had 82.53% of 5.1 μm particles and 12.00% of 11.0 μm particles in the presence of acoustics. FIG. 22 PANEL C shows that the central stream had 96.86% of 5.1 μm particles and 0.01% of 11.0 μm particles in the absence of acoustics. FIG. 22 PANEL D shows that the central stream had 46.36% of 5.1 μm particles and 52.73% of 11.0 μm particles in the absence of acoustics.

For the method combining acoustophoresis with acoustic fluid relocation, a minimum resonance acoustic field was 14.5 V. The flow rate for the lateral stream was 75 μL/min, and the flow rate for the central stream was 150 μL/min. Flow cytometry analysis showed that the percentage of the 11.0 μm particles was 82.58%. Acoustophoresis combined with acoustic fluid relocation was simpler and more convenient to use to separate binary mixtures of microparticles with sizes <12 μm with a difference in size of about 4-5 μm.

EMBODIMENTS

The following non-limiting embodiments provide illustrative examples of the invention, but do not limit the scope of the invention.

Embodiment 1

A method of separating a mixture of particles, the method comprising: 1) suspending the mixture of particles in a flow stream; 2) flowing the flow stream through a channel; and 3) subjecting the flow stream in the channel to a standing acoustic wave field, wherein the standing acoustic wave field subjects the flow stream to acoustophoresis and acoustic fluid relocation.

Embodiment 2

The method of embodiment 1, wherein the mixture of particles comprises particles greater than 1 μm in diameter and less than 1 μm in diameter.

Embodiment 3

The method of embodiment 1, wherein the mixture of particles comprises particles less than 1 μm in diameter.

Embodiment 4

The method of any one of embodiments 1-3, wherein the mixture of particles comprises red blood cells.

Embodiment 5

The method of any one of embodiments 1-4, further comprising producing the standing acoustic wave field by a piezoelectric transducer.

Embodiment 6

The method of any one of embodiments 1-4, further comprising producing the standing acoustic wave field by a waveform generator.

Embodiment 7

The method of any one of embodiments 1-6, wherein the standing acoustic wave field has a resonance frequency of about 500 KHz to about 10 MHz.

Embodiment 8

The method of any one of embodiments 1-7, wherein the standing acoustic wave field has a resonance frequency of about 2.91 MHz.

Embodiment 9

The method of any one of embodiments 1-8, wherein the acoustic fluid relocation has an acoustic frequency of about 2.5 MHz to about 3.5 MHz.

Embodiment 10

The method of any one of embodiments 1-9, wherein the acoustic frequency is about 3.31 MHz.

Embodiment 11

The method of any one of embodiments 1-10, wherein the mixture of particles comprises two types of biological particles.

Embodiment 12

The method of any one of embodiments 1-11, wherein the flow stream is flowed through the channel at a flow rate of about 50 µL/min to about 75 µL/min.

Embodiment 13

The method of any one of embodiments 1-12, wherein the channel has a trifurcated inlet with three inlet ports and a trifurcated outlet with three outlet ports.

Embodiment 14

The method of any one of embodiments 1-13, wherein the channel is about 200 µm wide.

Embodiment 15

The method of any one of embodiments 1-14, wherein the channel is about 100 µm deep.

Embodiment 16

The method of any one of embodiments 1-15, wherein the mixture of particles is suspended in a carrier.

Embodiment 17

The method of any one of embodiments 1-16, wherein the carrier is de-ionized water.

Embodiment 18

The method of any one of embodiments 1-16, wherein the carrier is phosphate buffered saline solution.

Embodiment 19

A device comprising: 1) a base slide, wherein the base slide comprises a top surface; 2) a connector, wherein the connector is attached to the top surface of the base slide; 3) an electrical component that produces an acoustic standing wave field, wherein the electrical component is attached to the top surface of the base slide; 4) a plate, wherein the plate comprises a top surface and a bottom surface, wherein the bottom surface of the plate is connected to the connector and the electrical component so that the plate is layered above the top surface of the base slide, wherein the top surface of the plate comprises a channel with an inlet end and an outlet end, wherein the inlet end comprises three inlet ports and the outlet end comprises three outlet ports, wherein the electrical component is positioned to transmit the acoustic standing wave field to the channel; and 5) a coverslide, wherein the coverslide is layered on the top surface of the plate, wherein the coverslide comprises six holes, wherein three holes are aligned with the three inlet ports and three holes are aligned with the three outlet ports.

Embodiment 20

The device of embodiment 19, wherein the base slide is a glass slide.

Embodiment 21

The device of any one of embodiments 19-20, wherein the device comprises at least two connectors, with each of the two connectors at opposite ends of the base slide.

Embodiment 22

The device of any one of embodiments 19-21, wherein the connector is made of poly(dimethylsiloxane).

Embodiment 23

The device of any one of embodiments 19-22, wherein the electrical component is a piezoelectric transducer.

Embodiment 24

The device of any one of embodiments 19-23, wherein the plate is a silicon wafer.

Embodiment 25

The device of any one of embodiments 19-24, wherein the channel is etched into the plate.

Embodiment 26

The device of any one of embodiments 19-25, wherein the plate is etched using deep reactive ion etching.

Embodiment 27

The device of any one of embodiments 19-26, wherein the channel is about 200 µm wide.

Embodiment 28

The device of any one of embodiments 19-27, wherein the channel is about 100 µm deep.

Embodiment 29

The device of any one of embodiments 19-28, wherein the coverslide is a glass coverslide.

Embodiment 30

The device of any one of embodiments 19-29, wherein the base slide, the plate, and the coverslide are about parallel.

Embodiment 31

The device of any one of embodiments 19-30, wherein the device further comprises three fluid ingresses and three fluid egresses, wherein the three fluid ingresses are connected to the three holes of the three inlet ports and the three fluid egresses are connected to the three holes of the three outlet ports.

Embodiment 32

The device of embodiment 31, wherein the three fluid ingresses and three fluid egresses are tubing.

Embodiment 33

The device of embodiment 32, wherein the tubing is silicon tubing.

Embodiment 34

The device of any one of embodiments 19-33, wherein the device is connected to an epi-fluorescence microscope.

Embodiment 35

The device of any one of embodiments 19-34, wherein the device is connected to a flow cytometer.

Embodiment 36

The device of any one of embodiments 19-35, wherein a portion of the bottom surface of the plate is under the channel, wherein the electrical component is connected to the portion of the bottom surface of the plate that is under the channel.

Embodiment 37

The device of any one of embodiments 19-36, wherein the base has a surface area, wherein the plate has a surface area that is no greater than the surface area of the base, and the coverslide has a surface area that is no greater than the surface area of the base.

Embodiment 38

A method of separating a mixture of particles, the method comprising: 1) suspending the mixture of particles in a flow stream; 2) flowing the flow stream through a channel of a device, the device comprising: a) a base slide, wherein the base slide comprises a top surface; b) a connector, wherein the connector is attached to the top surface of the base slide; c) an electrical component that produces an acoustic standing wave field, wherein the electrical component is attached to the top surface of the base slide; d) a plate, wherein the plate comprises a top surface and a bottom surface, wherein the bottom surface of the plate is connected to the connector and the electrical component so that the plate is layered above the top surface of the base slide, wherein the top surface of the plate comprises a channel with an inlet end and an outlet end, wherein the inlet end comprises three inlet ports and the outlet end comprises three outlet ports, wherein the electrical component is positioned to transmit the acoustic standing wave field to the channel; and e) a coverslide, wherein the coverslide is layered on the top surface of the plate, wherein the coverslide comprises six holes, wherein three holes are aligned with the three inlet ports and three holes are aligned with the three outlet ports; 3) subjecting the flow stream in the channel to the standing acoustic wave field, wherein the standing acoustic wave field subjects the flow stream to acoustophoresis and acoustic fluid relocation.

Embodiment 39

The method of embodiment 38, wherein the base slide is a glass slide.

Embodiment 40

The method of any one of embodiments 38-39, wherein the device comprises at least two connectors, with each of the two connectors at opposite ends of the base slide.

Embodiment 41

The method of any one of embodiments 38-40, wherein the connector is made of poly(dimethylsiloxane).

Embodiment 42

The method of any one of embodiments 38-41, wherein the electrical component is a piezoelectric transducer.

Embodiment 43

The method of any one of embodiments 38-42, wherein the plate is a silicon wafer.

Embodiment 44

The method of any one of embodiments 38-43, wherein the channel is etched into the plate.

Embodiment 45

The method of any one of embodiments 38-44, wherein the plate is etched using deep reactive ion etching.

Embodiment 46

The method of any one of embodiments 38-45, wherein the channel is about 200 μm wide.

Embodiment 47

The method of any one of embodiments 38-46, wherein the channel is about 100 μm deep.

Embodiment 48

The method of any one of embodiments 38-47, wherein the coverslide is a glass coverslide.

Embodiment 49

The method of any one of embodiments 38-48, wherein the base slide, the plate, and the coverslide are about parallel.

Embodiment 50

The method of any one of embodiments 38-49, wherein the device further comprises three fluid ingresses and three fluid egresses, wherein the three fluid ingresses are connected to the three holes of the three inlet ports and the three fluid egresses are connected to the three holes of the three outlet ports.

Embodiment 51

The method of embodiment 50, wherein the three fluid ingresses and three fluid egresses are tubing.

Embodiment 52

The method of embodiment 51, wherein the tubing is silicon tubing.

Embodiment 53

The method of any one of embodiments 38-52, wherein the device is connected to an epi-fluorescence microscope.

Embodiment 54

The method of any one of embodiments 38-53, wherein the device is connected to a flow cytometer.

Embodiment 55

The method of any one of embodiments 38-54, wherein the mixture of particles has a concentration of about 50,000 particles/mL to about 100,000 particles/mL.

Embodiment 56

The method of any one of embodiments 38-55, wherein the channel has a flow rate of about 50 µL/min to about 75 µL/min.

Embodiment 57

The method of any one of embodiments 38-56, wherein the channel has a flow rate of about 50 µL/min.

Embodiment 58

The method of any one of embodiments 38-57, wherein the channel has a flow rate of about 75 µL/min.

Embodiment 59

The method of any one of embodiments 38-58, wherein the mixture of particles is suspended in de-ionized water.

Embodiment 60

The method of any one of embodiments 38-58, wherein the mixture of particles is suspended in a phosphate buffered saline solution.

Embodiment 61

The method of any one of embodiments 38-60, wherein the mixture of particles comprises particles greater than 1 µm in diameter and less than 1 µm in diameter.

Embodiment 62

The method of any one of embodiments 38-60, wherein the mixture of particles comprises particles less than 1 µm in diameter and less than 1 µm in diameter.

Embodiment 63

The method of any one of embodiments 38-62, wherein the mixture of particles comprises red blood cells.

Embodiment 64

The method of any one of embodiments 38-63, wherein the standing acoustic wave field is amplified using a radiofrequency amplifier.

Embodiment 65

The method of embodiment 50, wherein the three fluid ingresses comprise a first lateral ingress, a central ingress, and a second lateral ingress, and wherein the three fluid egresses comprise a first lateral egress, a central egress, and a second lateral egress, wherein the mixture of particles is flowed through the first lateral ingress and the second lateral ingress into the channel, and wherein a carrier is flowed through the central ingress into the channel, wherein a first component from the mixture of particles flows from the channel to the first lateral egress and the second lateral egress, and flows out of the first lateral egress and second lateral egress, and wherein a second component from the mixture of particles flows from the channel to the central egress, and flows out of the central egress.

Embodiment 66

The method of embodiment 65, wherein the carrier is de-ionized water.

Embodiment 67

The method of embodiment 65, wherein the carrier is phosphate buffered saline solution.

Embodiment 68

The method of any one of embodiments 38-67, wherein the standing acoustic wave field has a resonance frequency of about 500 KHz to about 10 MHz.

Embodiment 69

The method of any one of embodiments 38-68, wherein the standing acoustic wave field has a resonance frequency of about 2.91 MHz.

Embodiment 70

The method of any one of embodiments 38-69, wherein the standing acoustic wave field has an acoustic frequency of 2.5 MHz to about 3.5 MHz.

Embodiment 71

The method of embodiment 70, wherein the acoustic frequency is about 3.31 MHz.

What is claimed is:

1. A method of separating a mixture of particles, the method comprising:
   1) suspending the mixture of particles in a flow stream, wherein the mixture of particles comprises a population of first particles and a population of second particles, wherein the population of first particles has a first mean diameter, and the population of second particles has a second mean diameter, and wherein the first mean diameter is greater than is the second mean diameter;

2) flowing the flow stream through a channel;

3) concurrently with the flowing the flow stream through the channel, flowing a first pair of lateral streams through the channel, wherein each lateral stream of the first pair of lateral streams independently comprises a carrier fluid, wherein the flow stream is in contact with the first pair of lateral streams, and each lateral stream of the first pair of lateral streams is not in contact with the other lateral stream of the first pair of lateral streams; and 4) subjecting the flow stream and the first pair of lateral streams in the channel to a standing acoustic wave field, wherein the standing acoustic wave field subjects the flow stream and the first pair of lateral streams to acoustophoresis and acoustic fluid relocation, wherein the standing acoustic wave field relocates the first pair of lateral streams to form a central flow stream, wherein the standing acoustic wave field splits and relocates the flow stream to a second pair of lateral streams, wherein the population of first particles remains in the central flow stream, and the population of second particles relocates to the second pair of lateral streams in the channel.

2. The method of claim 1, wherein the first mean diameter is greater than 1 μm in diameter and the second mean diameter is less than 1 μm in diameter.

3. The method of claim 1, wherein the first mean diameter is less than 1 μm.

4. The method of claim 1, wherein the mixture of particles comprises red blood cells.

5. The method of claim 1, further comprising producing the standing acoustic wave field by a piezoelectric transducer.

6. The method of claim 1, further comprising producing the standing acoustic wave field by a waveform generator.

7. The method of claim 1, wherein the standing acoustic wave field has a resonance frequency of about 500 KHz to about 10 MHz.

8. The method of claim 7, wherein the standing acoustic wave field has a resonance frequency of about 2.91 MHz.

9. The method of claim 1, wherein the acoustic fluid relocation has an acoustic frequency of about 2.5 MHz to about 3.5 MHz.

10. The method of claim 9, wherein the acoustic frequency is about 3.31 MHz.

11. The method of claim 1, wherein the mixture of particles comprises two types of biological particles.

12. The method of claim 1, the flow stream is flowed through the channel at a flow rate of about 5 μL/min to about 500 μL/min.

13. The method of claim 1, wherein the channel has a trifurcated inlet with three inlet ports and a trifurcated outlet with three outlet ports.

14. The method of claim 1, wherein the channel has a width of about 50 μm to about 300 μm.

15. The method of claim 1, wherein the channel has a depth of about 20 μm to about 200 μm.

16. The method of claim 1, wherein the mixture of particles is suspended in the flow stream, wherein the flow stream is de-ionized water, a salt solution, or comprises a biological buffer.

17. The method of claim 16, wherein the flow stream is de-ionized water.

18. The method of claim 16, wherein the flow stream is buffered saline solution.

19. The method of claim 1, wherein the flow stream is between the first pair of lateral streams.

* * * * *